United States Patent [19]
Morgan et al.

[11] Patent Number: 5,446,157
[45] Date of Patent: Aug. 29, 1995

[54] BORON DIFLUORIDE COMPOUNDS USEFUL IN PHOTODYNAMIC THERAPY AND PRODUCTION OF LASER LIGHT

[76] Inventors: Lee R. Morgan, 725 Topaz St., New Orleans, La. 70124; Joseph H. Boyer, 829 Barracks St., New Orleans, La. 70116

[21] Appl. No.: 20,293

[22] Filed: Feb. 19, 1993

Related U.S. Application Data

[63] Continuation-in-part of Ser. No. 513,059, Apr. 23, 1990, Pat. No. 5,189,029.

[51] Int. Cl.$^6$ .............................................. C07F 5/02
[52] U.S. Cl. ..................................... 546/13; 548/110; 548/405
[58] Field of Search .................. 514/64; 548/405, 110; 546/13

[56] References Cited

U.S. PATENT DOCUMENTS

| | | | |
|---|---|---|---|
| 4,774,339 | 9/1988 | Haugland et al. | 548/405 |
| 4,799,230 | 1/1989 | Boyer | 372/53 |
| 5,187,288 | 2/1993 | Kang et al. | 548/110 |
| 5,248,782 | 9/1993 | Haugland et al. | 548/110 |
| 5,274,113 | 12/1993 | Kang et al. | 548/405 |
| 5,338,854 | 8/1994 | Kang et al. | 548/110 |

FOREIGN PATENT DOCUMENTS 0210351 4/1986 European Pat. Off. .
WO87/04071 7/1687 WIPO .

OTHER PUBLICATIONS

Triebs et al, Chemical Abstracts, vol. 70 (1969) 37589u.
Falk et al, Chemical Abstracts, vol. 92 (1980) 75389s.
Wories, H. J., "A Novel Water–Soluble Fluorescent Probe: Synthesis, Luminescence, and Biological Properties of the Sodium Salt of the 3,3′,5,5′-tetramethyl-2,2′-pyrromethene-1,1′-BF$^2$ Complex", Recueil Des. Travaus Chemiques des Pays–Bas, 104/11, (Nov. 1985), pp. 288–291.
Pavlopoulos, Theodore G.; Sha, Mayur and Boyer, Joseph H., "Laser Action From a Tetramethylpyrromethene-BF$^2$ Complex" Applied Optics, vol. 27, No. 24, pp. 4998–4999 (Dec. 1988).
E. Vos de Wael, et al., "Pyrromethene-BF$_2$ complexes (4,4′-difluoro-4-bora-3a,4a-diaza-s-indacenes). Synthesis and luminescence properties", *J. of the Royal Netherlands Chemical Society*, 96:306–309 (1977).
Chemical Abstracts 111:47646r (1989), "Efficient laser action from 1,3,5,7,8-pentamethyl-pyrromethene-boron difluoride complex and its disodium 2,6-disulfonate derivative."
Chemical Abstracts 111:123190e (1989), "Quasiaromatic heterocyclics as laser dyes."
Basting et al., "New Laser Dyes," App. Phys. 3:81–88 (1976).
American Association for Cancer Research Abstract 30:576 (1989) #2292.

*Primary Examiner*—Richard L. Raymond
*Attorney, Agent, or Firm*—Klarquist Sparkman Campbell Leigh & Whinston

[57] ABSTRACT

A new group of fluorescent organic compounds having a variety of uses are described. They are especially useful as dye compounds in dye laser systems, and as photochemical agents in the treatment of diseased tissues using photodynamic therapy techniques. The compounds include a tri-cyclic compound having the following structure:

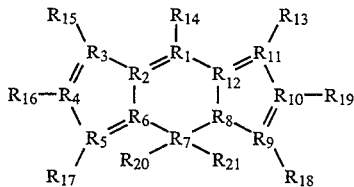

Preferably $R_1$-$R_5$=$R_9$-$R_{12}$=C; $R_7$=B; $R_6$ and $R_8$=N; $R_{14}$=lower n-alkyl or an electron withdrawing group such as CN$^-$; $R_{16}$ and $R_{19}$ are independently selected from the group consisting of lower n-alkyl, a sulfate or an acid or salt thereof, or hydrogen; and $R_{20}$=$R_{21}$=F. Other compounds include compounds of the formula (Abstract continued on next page.)

5,446,157
Page 2
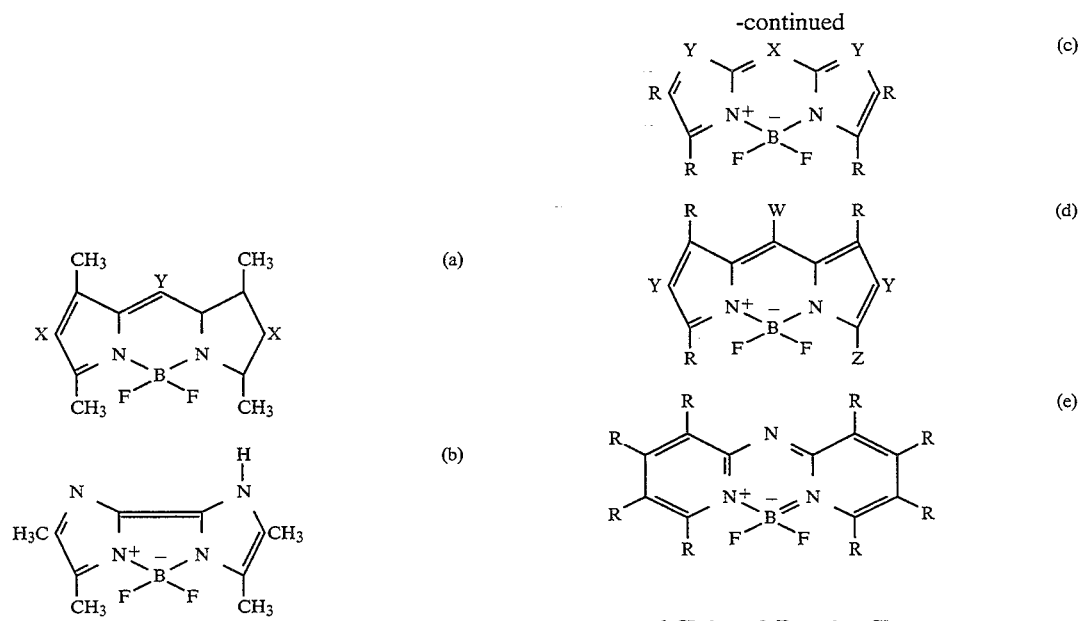
6 Claims, 3 Drawing Sheets

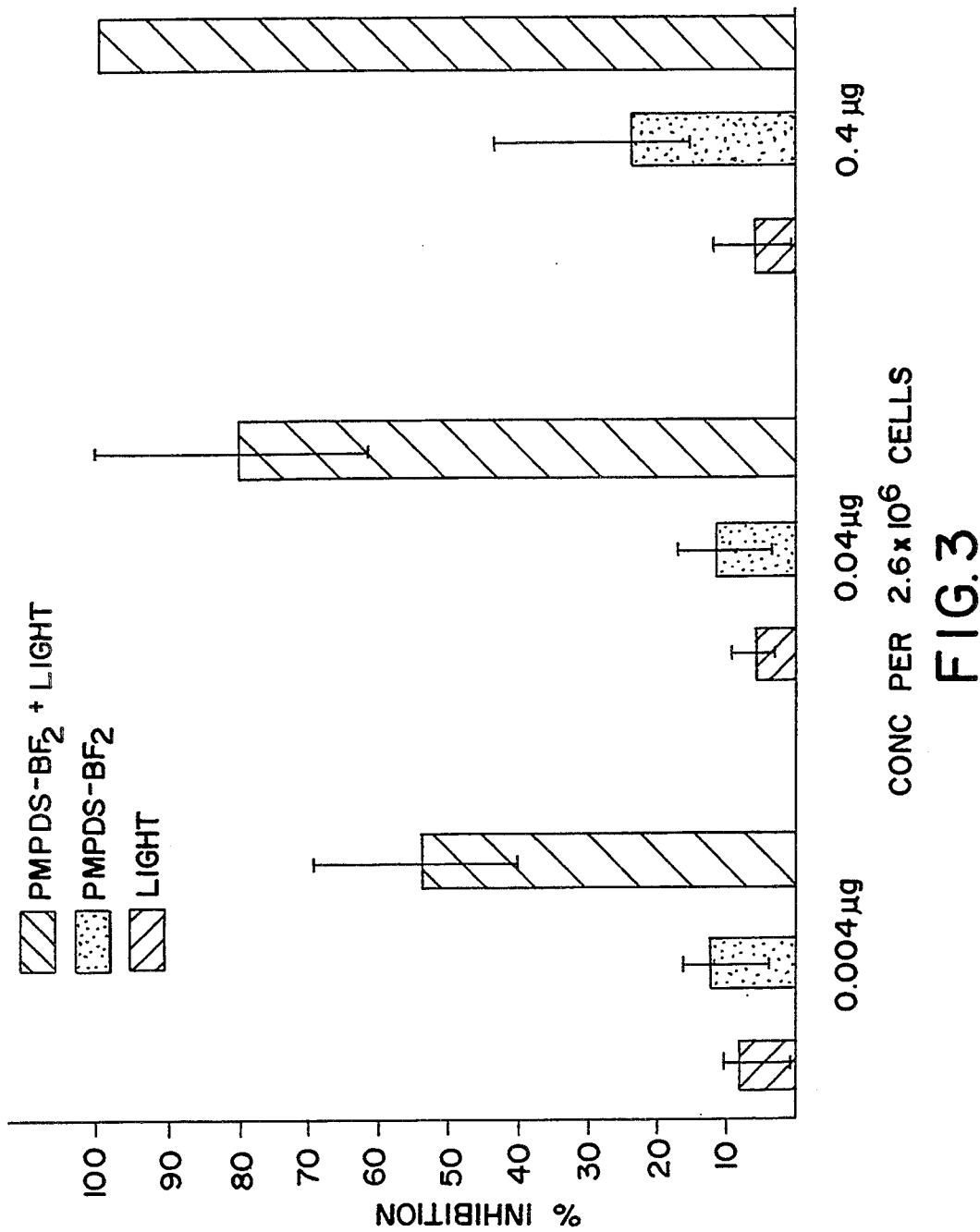

BORON DIFLUORIDE COMPOUNDS USEFUL IN PHOTODYNAMIC THERAPY AND PRODUCTION OF LASER LIGHT

ACKNOWLEDGEMENT OF GOVERNMENT SUPPORT

This invention was made partially with government support under Grant No. ONR (N00014-87-K-0254) awarded by the Department of the Navy, Office of the Chief of Naval Research. The U.S. Government may have certain rights in this invention.

CROSS-REFERENCE TO RELATED APPLICATION

This is a continuation in part of United States patent application Ser. No. 07/513,059 filed Apr. 23, 1990, now U.S. Pat. No. 5,189,029.

BACKGROUND OF THE INVENTION

1. Field of the Invention

The present invention generally relates to chemical compounds and compositions that are useful as laser dyes and in photodynamic therapy.

2. General Discussion of the Background

A demand currently exists for chemical compounds having a high degree of stability and quantum fluorescence yield. These materials are usable for numerous purposes, including the generation of laser light. Substantial research has been conducted involving chemical laser systems capable of operating in the near UV/-visible/near IR spectral regions. Dye lasers offer the greatest promise in meeting these requirements.

In the late 1960s, organic dye lasers tunable over a wide frequency range were developed. The light beams produced by these lasers were capable of being concentrated into an extremely narrow band through the use of diffraction gradient systems or other optical devices. Today, dye lasers are used for a variety of purposes in numerous technical fields including medicine and applied physics. For example, they may be used to conduct spectral analysis of chemical compounds. Also, they are useful in facilitating the analysis of photosynthetic and biomolecular reaction processes. Dye lasers in the medical field are used for numerous applications including cancer therapy, ophthalmological studies, surgeries and the like.

Typically, the lasing materials used in dye laser systems consist of fluorescent organic dye compounds dissolved in a liquid solvent. As discussed in Laurence, C. L., *The Laser Book—A New Technology of Light*, Prentice Hall Press, New York, 1986, one of the most important capabilities of dye lasers is their high degree of wavelength tunability. For example, the wavelength output of conventional dye lasers may be scanned over a 10–40 nm range. Through the use of different dye types, laser light output can be achieved at wavelengths from near ultraviolet to near infrared. Dye lasers are capable of being tuned because the chemical dyes which they use have specific vibrational and rotational energy levels which can be characterized.

Laser dye efficiency, laser action threshold, and flashlamp performance are closely inter-related. Desirable excitation from a large flashlamp with a slow risetime requires (1) lower triplet-triplet (T—T) absorption of the laser dye over its fluorescence region $\eta_T(\lambda_F)$, (2) shorter triplet state (phosphorescence) lifetime $\tau_p$, and (3) laser dye quantum fluorescence yield close to unity ($\Theta$ near 1). (Drexhage in *Dye Lasers*, Springer Verlag, 1977.) Most of the commercially available and generally used dye molecules accumulate in their triplet state due to intersystem crossing when they are excited by a light source. Many commercially available laser dyes also unfortunately show T—T absorption in the spectral region of their laser action. Other problems with existing laser dyes include poor photostability and thermal stability, and relatively low solubility.

The selection of dyes for use in dye lasers is presently accomplished by trial and error. Numerous organic compounds showing strong fluorescence have been synthesized and are commercially available. However, very few of these materials are suitable for use in dye lasers. Most commercially used laser dyes primarily consist of coumarin and rhodamine compositions. These dyes, along with other commercially available materials, have only moderate energies and relatively high degrees of photodecomposition. In addition, many dyes require excitation using flashlamp systems with steep risetimes of 1 microsecond or less. Flashlamps meeting these requirements are difficult to construct for operation above 200 Joules.

Chelation of aluminum dichloride by a pyrromethene bidentate ligand has been reported to give an unstable orange solid; light absorption and emission data have not been reported for this compound. Treibs and Kreuzer, *Liebigs Ann. Chem.*, 718:208, 1968; 721:116, 1969. Pyrromethene (P)-metal (M) chelates (P$_2$M) of tetracoordinate zinc, nickel, and copper have shown weak fluorescence above 500 nm ($\Theta \sim 10^{-3}$). Falk et al., *Monatsh. Chem.*, 718:208, 1968; 721:116, 1969. However, fluorescence is not important for laser activity. Pyrazoboles (dimeric 1-borylpyrazole chelates of dialkylboron (BR$_2$)) and the BF$_2$ complexes of 1,2,3,4-tetrahydro-1,10-phenanthroline have not been found to be fluorescent. Trofimenko, *J. Amer. Chem. Soc.*, 89:3165–3170, 1967; 92:5118, 1970; Klebe, et al., *Chem. Ber.* 116:3125, 1983.

Modest laser activity ($\lambda_{las}$ 420 nm) was reported for a "boratriazinium" salt by Basting et al., *Appl. Phys.*, 3:81, 1974, however the structure was not established.

Another important use for fluorescent dye compositions involves the detection and treatment of diseased tissues using photodynamic therapy (PDT) techniques. These techniques, traditionally involving the administration of a photosensitizing drug to a patient, result in the distribution of a drug throughout the patient's body. The drugs or chemicals subsequently localize in areas of diseased tissue which is then illuminated with light of an appropriate wavelength to activate the drugs or chemicals. This photoactivation results in photochemical reactions in the diseased tissues that ultimately cause cytotoxic injury and/or death to the tissues.

There are currently two generally proposed mechanisms by which photosensitizing drugs are chemically altered upon illumination by an appropriate light source. The first mechanism (Type I) typically involves hydrogen atom abstraction from the drugs, thereby producing free radicals. Subsequent reactions of the radical products with other organic molecules or with oxygen results in biochemical destruction of the diseased tissue.

The other reaction mechanism (Type II) normally involves energy transfer from the electronically excited drugs to oxygen, producing singlet molecular oxygen which consequently reacts with a variety of substrates to produce oxygenated products. This pathway can also result in electron transfer from the excited drug to oxygen, producing an oxidized drug product in combination with superoxide ions. This reaction mechanism, along with the first mechanism described above, is schematically presented in the following formula:

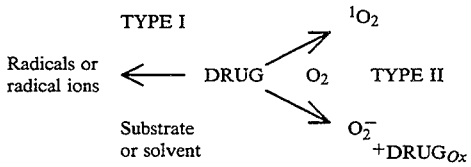

Photodynamic therapy has been used experimentally in cancer patients since 1972. One experimental drug known as Photofrin II (a purified version of hematoporphyrin) has undergone randomized clinical trials in photodynamic therapy. Other photosensitizing drugs used in photodynamic therapy procedures include phyhalocyanines (merocyanine 540), substituted prupurines, xanthenes (Rhodamine 123 6G&B) cationic cyanine dyes, chlorine polymers, chalcogenapyrylium dyes containing selenium or tellurium atoms in the chromophore, phenothiazinium derivatives, benzophenoxoniums (Nile Blue A) and triarylmethanes (Victoria Blue BO [VB-BO]). The exact mechanisms used by the above chemicals to destroy diseased tissues (including cancer cells) upon exposure to an excitory light source is currently unknown. Moreover, the efficacy of these and other currently used chemicals in photodynamic therapy has not been entirely substantiated, although positive results have been demonstrated in many instances.

Ongoing research has involved a search for photochemicals of improved stability which express minimal side effects. A major side effect caused by currently used drugs is the development of uncontrolled photosensitivity reactions in patients after systemic drug administration. Upon exposure to the sun, patients develop generalized skin photosensitization. Ongoing research has specifically involved a search for chemicals which avoid these side reactions.

As described above, numerous chemicals have been synthesized which show strong fluorescence and potential value as photosensitizing drugs. "Fluorescence" as used herein is defined as a spontaneous random emission of light resulting from the transition of a molecule from the excited singlet state ($S_1$) to the ground state ($S_0$). Many photochemical reactions arise from the triplet state ($T_1$). However, most photochemical drugs accumulate in a triplet state due to intersystem crossing. These triplet molecules consequently absorb light more or less efficiently, depending on the magnitude of their triplet state absorption and concentration.

Thus, a need exists for photosensitizing chemicals which are useful in photodynamic therapy characterized by reduced triplet-triplet (T—T) absorption upon the application of light from an external source. Moreover, a need exists for photosensitizing drugs which are easily activated and are photochemically stable. The present invention satisfies this need, as described below.

It is an object of the present invention to provide improved organic chemicals that are cytotoxic when illuminated.

It is another object of the invention to provide improved organic chemicals that are suitable for use as laser dyes.

It is another object of the invention to provide improved laser dyes that offer a high degree of photochemical stability.

It is another object of the invention to provide improved laser dyes that are readily dissolvable and easy to use.

It is another object of the invention to provide improved laser dyes that offer a high fluorescence quantum efficiency ($Q_F > 0.7$).

It is another object of the invention to provide improved laser dyes with low triplet-triplet (T—T) absorption, thereby enabling the use of flashlamp pumping systems having slower risetimes.

It is another object of the invention to provide improved laser dyes which produce laser light having a higher intensity in comparison with the light beams produced using conventional dyes.

It is another object of the invention to provide an improved method for photodynamic therapy, particularly using chemicals which are stable, readily soluble and easily prepared.

An even further object of the invention is to provide an improved photodynamic therapy method using photosensitizing chemicals having reduced T—T absorption with a minimum overlap of fluorescence emission and that are cytotoxic.

SUMMARY OF THE INVENTION

The present invention involves improved laser dye compositions which are superior to previously used dyes in a variety of ways. Primarily, the dyes described herein have reduced T—T absorption and a lower laser action threshold. This enables the use of flashlamps with slower risetimes. These flashlamps have a longer functional life because they operate at lower driving voltages. Furthermore, a more efficient conversion of the flashlamp pump light due to reduced T—T absorption enables the production of a higher intensity laser beam. Finally, the dyes described herein have improved photochemical stabilities which result in reduced degradation of the dye materials.

In accordance with the foregoing objects, a new group of organic materials having a wide variety of uses is disclosed. The materials are especially useful as dye compounds in dye laser systems, and as photochemical cytotoxic agents in the treatment of diseased tissues using photodynamic therapy techniques. The materials described herein involve a substituted tri-cyclic compound having the following structures:

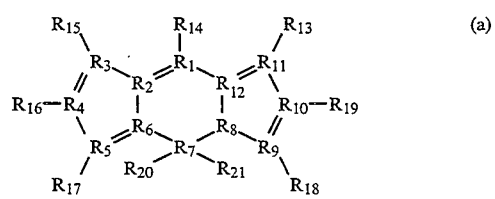

wherein $R_1$ is selected from the group consisting of C, N, B, preferably C and N, most preferably C;

$R_2$, $R_3$, $R_5$, $R_6$, $R_8$, $R_9$, $R_{11}$, and $R_{12}$ are independently selected from the group consisting of C and N, wherein R₆ and R₈ are preferably N, and R₂, R₃, R₅, R₉, R₁₁ and R₁₂ are preferably C;

R₄ and R₁₀ are independently selected from the group consisting of C, N, O, and S, preferably C;

R₇ is selected from the group consisting of C, N, B, preferably B;

R₁₃–R₁₉ are selected from the group consisting of H, F, Cl, Br, I, CN, NC, NO, NO₂, NH₂, NCO, CO₂H, CONH₂, phenyl, naphthyl, pyrryl, pyrazolyl, triazolyl, tetrazolyl, oxazolyl, isoxazolyl, thiazolyl, isothiazolyl, ArF, ArN₂, and NHCOAr where Ar=phenyl or naphthyl, $C_nH_{2n+1}$, where $n$ is an integer from 1 to 4, preferably 2 to 4, $C_nF_{2n+1}$, $C_nH_{2n}F_{2n+1}$, $(C_nF_{2n+1})CO$, $CO_2C_2F_{2n+1}$, $(CH_2)_nF$, $(CH_2)_nCl$, $(CH_2)_nBr$, $(CH_2)_nI$, $(CH_2)_nCN$, $(CH_2)_nNC$, $(CH_2)_nNO_2$, $(CH_2)_nNO$, $(CH_2)_nCO(C_nF_{2n+1})$, $(CH_2)_nCO_2H$, and $(CH_2)_nNH_2$, where n is an integer from 1 to 3, SO₃M and CO₂M where M is Na or K, cyclic alkyl groups having the formula $C_nH_{2n-1}$ where n is an integer from 4 to 6, $C_nH_{2n-2}$ and olefin derivatives having the formula $C_nH_{2n-1}$ where n is an integer from 2 to 4, RCO, CO₂R, CONHR, CON(R)₂, NHR, N(R)₂, NHCOR, C(NOR)R, SO₃R, SO₂R, PO₃R, $(CH_2)_nCOR$, $(CH_2)_nSO_3R$, $(CH_2)_nSO_2R$, $(CH_2)_nNHR$, $(CH_2)_nN(R)_2$, and $(CH_2)_nNHCOR$ where $R=C_nH_{2n+1}$ and n is an integer from 1 to 4, $C_nH_{2n-m}$ where n is an integer from 2 to 4 and m is an integer from 2 to 4, $(CH_2)_nAr$, $(CH_2)_nArN_2$, and $(CH_2)_nNHCOAr$ where Ar=phenyl or naphthyl and n is an integer from 1 to 4, $(CH_2)_nHET$ where Het=pyrryl, pyrazolyl, triazolyl, tetrazolyl, oxazolyl, isoxazolyl, thiazolyl, or isothiazolyl and n is an integer from 1 to 3, and $(CH_2)_nSO_3M$ where M=Na or K and n is an integer from 1 to 4;

R₂₀ and R₂₁ are independently selected from the group consisting of H, F, phenyl, naphthyl, and $C_nH_{2n+1}$ where n is an integer from 1 to 4, and R₂₀ and R₂₁ are preferably F; and wherein R₁₃, R₁₄, R₁₇ and R₁₈ are all preferably lower t-alkyl or n-alkyl, most preferably methyl or ethyl, and R₁₆ and R₁₉ may also be lower t-alkyl or n-alkyl, and R₁–R₂₁ can be any subgroup of the listed substituents.

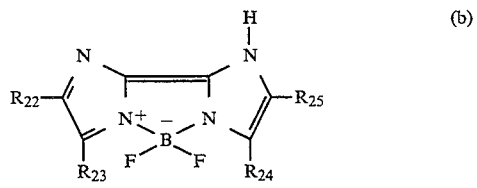

(b)

wherein R₂₂–R₂₅ are lower t-alkyl or n-alkyl, preferably ethyl and/or t-butyl/n-butyl.

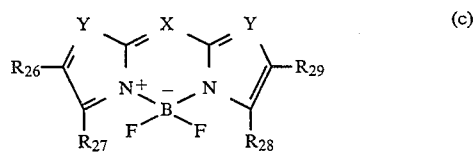

(c)

wherein R₂₆–R₂₉ are H or lower t-alkyl or n-alkyl, preferably lower n-alkyl, and wherein X=CH or N, or C substituted (for example with an alkyl substitution) preferably CH; and Y=CH or N or C substituted (for example with an alkyl substitution), preferably CH; or

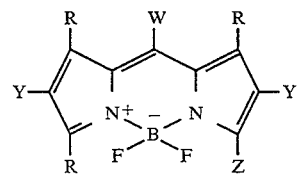

(d)

wherein R=lower t-alkyl or n-alkyl or CN; W=lower t-alkyl or n-alkyl or CN; Y=lower t-alkyl or n-alkyl or CH=CHCN; and Z=lower t-alkyl or n-alkyl or CH=CHCN.

Particularly preferred compounds include (b), (c) or (d), or any combination thereof.

Especially preferred embodiments include

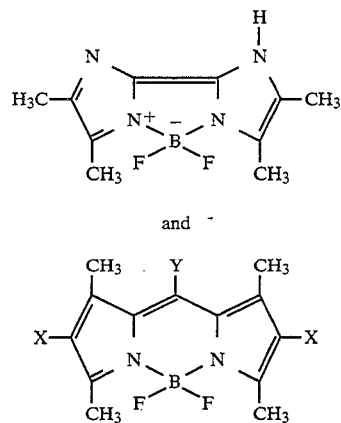

and wherein X is lower alkyl or sulfonate (or pharmaceutically acceptable sulfate salts), or more preferably lower t-alkyl or n-alkyl, and Y is lower alkyl, more preferably lower t-alkyl or n-alkyl, for example methyl, ethyl, propyl or butyl.

Examples of other compounds that can be used in the method of the present invention are those already disclosed in U.S. patent application Ser. No. 07/513,059, now U.S. Pat. No. 5,189,029, which is incorporated by reference:

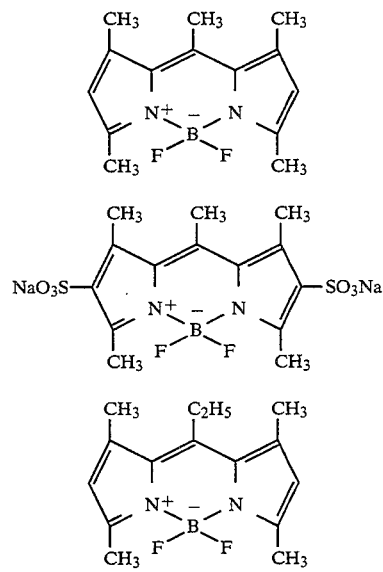

Using the method of the present invention, cytotoxic injury is induced in targeted tissue by introducing the compound into or adjacent the targeted tissue. After the compound is administered, the targeted tissue is exposed to a sufficient amount of light of a sufficient wavelength for a sufficient period of time to cause injury to the targeted tissue. The compound may be administered to the subject by systemic (for example, intravenous) administration, local injection into the target tissue, or topical application to the target tissue. The targeted tissue may be exposed to a light source such as a laser, a sun lamp, or a fiber optic illumination system, such as an endoscope.

These and other objects, features, and advantages of the invention will be described below in the following detailed description of preferred embodiments and accompanying examples.

BRIEF DESCRIPTION OF THE DRAWINGS

FIG. 3 is a bar graph showing the percentage inhibition of growth of human ovarian tumor cells in vitro following treatment of the cells with a compound of the present invention and exposure to light.

DETAILED DESCRIPTION OF SEVERAL PREFERRED EMBODIMENTS

Figure 1:
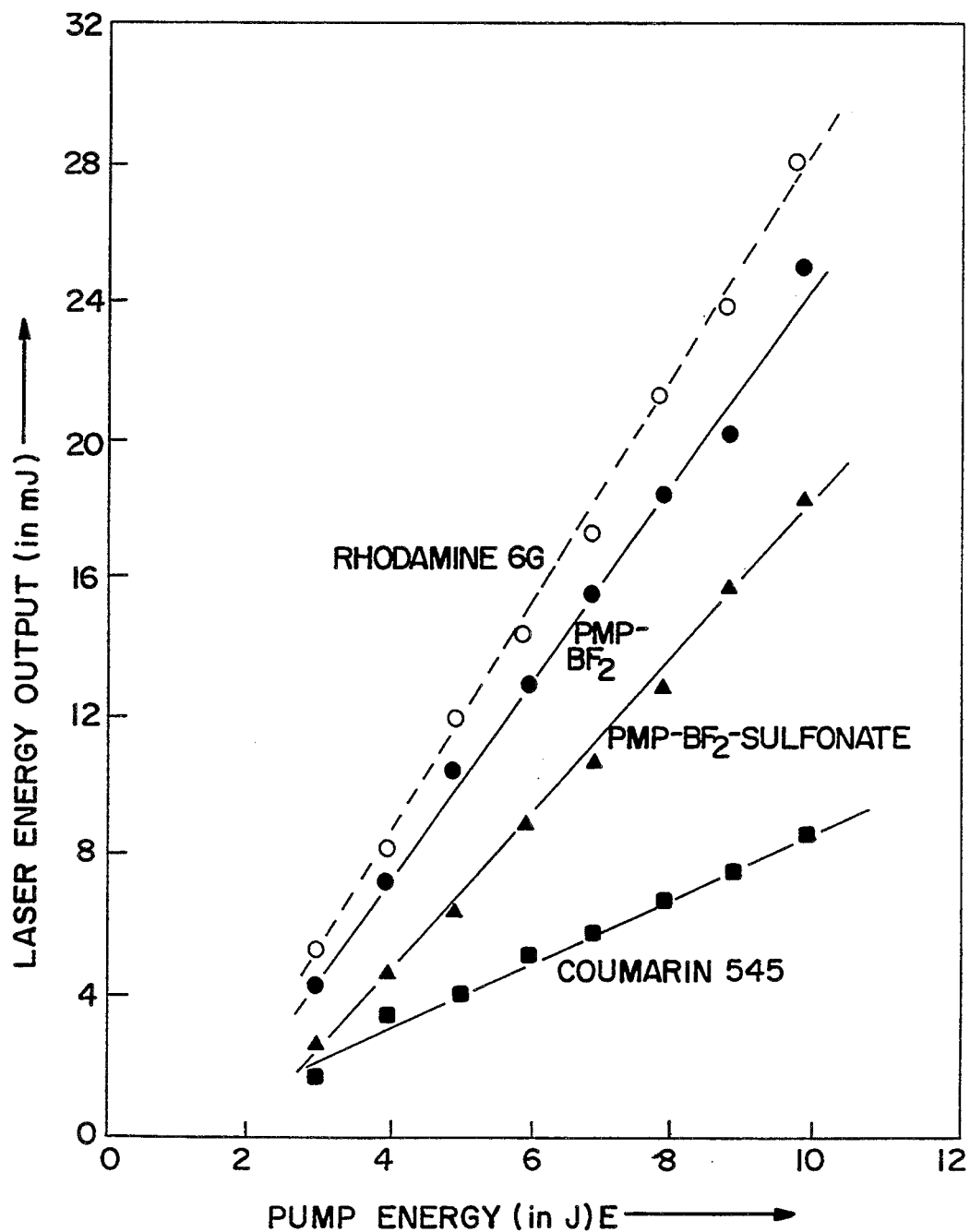
FIG. 1 is a graph of laser energy output as a function of energy for several compounds of the invention (4,4-difluoro-1,3,5,7,8-pentamethyl-4-bora-3a,4a-diaza-s-indacene and the disodium salt of 4,4-difluoro-1,3,5,7,8 pentamethyl-4-bora-3a,4a-diaza-s-indacene-2,6 disulfonic acid monohydrate) in comparison with previously known laser dyes (Rhodamine 6G and Coumarin 545).

In accordance with the present invention, improved chemical compounds and compositions are disclosed which have a variety of uses. They are especially useful as dye media in laser systems, and as photochemical agents in photodynamic therapy techniques. In dye laser systems, many of the compounds have a power output, photostability and solubility that is superior to currently available dyes, including coumarin and rhodamine-based compositions. When used in photodynamic therapy techniques, they are highly effective in destroying targeted tissues.

The basic chemical tri-cyclic structure of one class of the compositions described herein is as follows:

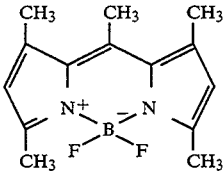

wherein preferred substituents are those listed in the Summary of the Invention. Several specific examples of these compounds are given in Examples I–III.

EXAMPLE I

In this example, the tricyclic structure shown above has the following substitution pattern:

$R_1$–$R_5$ = C  $R_{13}$–$R_{15}$ = $CH_3$
$R_6$ = $R_8$ = N
$R_7$ = B  $R_{17}$–$R_{18}$ = $CH_3$
$R_9$–$R_{12}$ = C
$R_{16}$ = $R_{19}$ = H  $R_{20}$–$R_{21}$ = F

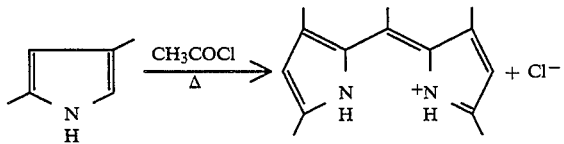

(4,4-difluoro-1,3,5,7,8-pentamethyl 4-bora-3a,4a-diaza-s-indacene).

To prepare this material, 2,4 dimethylpyrrole (2 g, 0,021 moles) was combined with freshly distilled acetyl chloride (18 ml) which was added drop-wise. This initial reaction and its intermediate product is shown as follows:

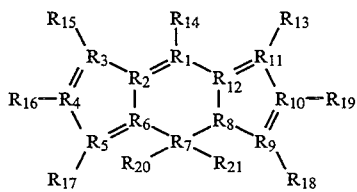

The above reaction was exothermic, and resulted in the production of a chemical mixture having a dark red color. The mixture was then heated under reflux for approximately 2 hours, followed by distillation and removal of excess acetyl chloride. The residue was treated with pentane, stirred for approximately 10 minutes at room temperature, and pentane was decanted. The residue was triturated with pentane (approximately 50 ml) for about 1 hour. A black, finely divided solid was removed, washed with approximately 10 ml of pentane, dried in air, and then dried in a desiccator under vacuum for about 2 hours. This material, which represents the intermediate product of the above reaction (pentamethylpyrromethene hydrochloride), weighed approximately 2.5 grams and had a melting point of 180°–182° C.

Next, the pentamethylpyrromethene hydrochloride (2.5 grams, 0.01 moles) was dissolved in 350 ml of benzene. Triethyl amine (9.6 grams, 0.095 moles) was then added to the dissolved pentamethylpyrromethene hydrochloride, and the mixture stirred at room temperature for about 10 minutes. The reaction flask containing these materials was subsequently purged with nitrogen. Boron trifluoride etherate (16 ml, 0.13N) was added drop-wise over a period of 5 minutes. The mixture was heated under reflux for about 20 minutes, allowed to cool to room temperature, washed with three 100 ml portions of water, and dried over magnesium sulfate. The brownish-red solid product was purified by flash column chromatography over silica eluted with 60:40 benzene/pentane. This resulted in green-yellow fluorescent fractions which were subsequently combined and concentrated to a reddish-orange solid (2.1 grams). The solid recrystallized from ethyl acetate to give 1.7 grams of product (4,4-difluoro-1,3,5,7,8-pentamethyl-4-bora-3a,4a-diaza-s-indacene [$C_{14}H_{17}BF_2N_2$] m.p.=255°–257° C.). A schematic summary of the manufacturing steps used to produce the product from pentamethylpyrromethene hydrochloride is illustrated in the following reaction:

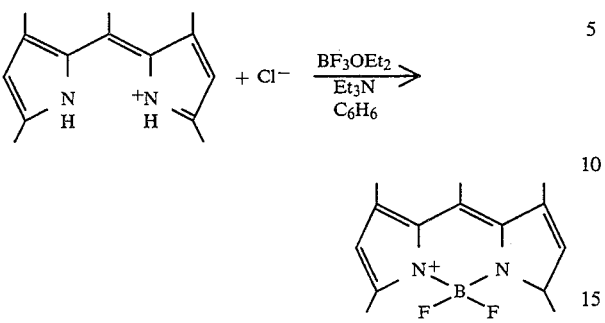

The foregoing procedure resulted in a 69% product yield. With respect to use of the product as a laser dye, it has a lasing threshold of 9.5 kV, with a lasing wavelength range of approximately 532–565 nm. This data was obtained using a 60 mg quantity of product dissolved in 250 ml of methanol in a 10 mm flashlamp D-1100 dye laser manufactured by the Phas-R Company of New Durham, N.H. (Model D-1100).

Figure 2:
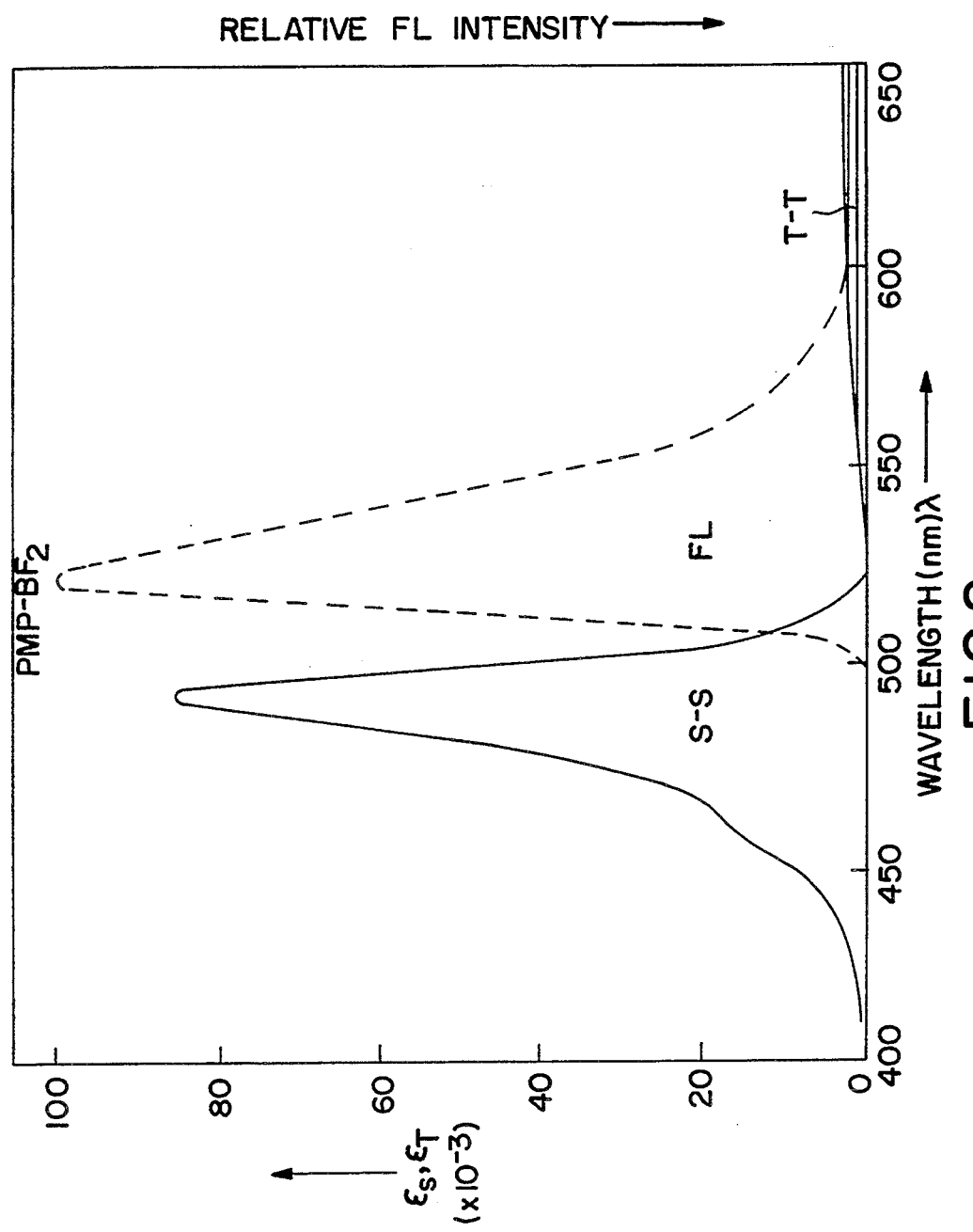
FIG. 2 is a graph representing the absorption and fluorescence spectra of a compound of the invention (4,4-difluoro-1,3,5,7,8-pentamethyl-4-bora-3a,4a-diaza-s-indacene) dissolved in ethanol.

FIG. 2 shows the absorption (S—S) and fluorescence (FL) spectra of the compound of Example I (designated PMP-BF$_2$) dissolved in ethanol. The T—T absorption spectrum was recorded at 77K, employing a $1 \times 10^{-4}$ molar solution of 2-methyltetrahydrofuran as solvent.

In addition, tests were conducted on the product in order to determine its solubility/fluorescence in various solvents. One property of the compositions described herein involves a variable degree of solubility/fluorescence relative to the solvents with which they are combined. Data showing a variety of different solvents combined with the product of Example I is presented below in Table I:

TABLE I

| Solvent | Solubility | Color of Solution | Fluorescence Room light | Fluorescence UV |
|---|---|---|---|---|
| $CH_2Cl_2$ | soluble | yellowish green | yellowish green | yellowish green |
| $CH_3CO_2C_2H_5$ | partly soluble | brownish orange | yellowish green | yellowish green |
| $O(CH_2CH_2)_2O$ | partly soluble | yellowish green | yellowish green | yellowish green |
| $CH_3C\equiv N$ | partly soluble | yellowish green | yellowish green | yellowish green |
| $C_2H_5OH(95\%)$ | partly soluble | yellowish green | yellowish green | yellowish green |
| $CF_3CH_2OH$ | partly soluble | green | yellowish green | yellowish green |
| $(CF_3)_2CHOH$ | soluble | yellow | green | green |
| $CClF_2—CFCl_2$ | slightly soluble | yellow | green | green |
| $H_2O$ | insoluble | — | — | — |

In addition, experiments were conducted in order to determine the photostability of the product of Example I. A solution was prepared by mixing 0.1 g of the product with 50 ml of dichloromethane solvent. The solution was placed in a 100 ml round bottom flask and irradiated with light from a sun lamp (250 watts at a distance of approximately 8 inches from the flask). No visual change in fluorescence was observed over a period of 22 days. However, another solution was made by combining 0.1 g of product in 250 ml of $CH_3OH$ and 10 ml of $CH_2Cl_2$. Addition of the $CH_2Cl_2$ was undertaken to obtain complete dissolution. The solution was placed in a 250 ml round bottom flask and irradiated as described above. After 8 days, no fluorescence was observed. Thus, the use of different solvents will cause a variation in both the character and duration of fluorescence.

EXAMPLE II

In this example, the tricyclic structure given above has the same substitutions as in Example I, but $R_{16}=R_{19}=SO_3^{-2}$ (as $SO_3Na$).

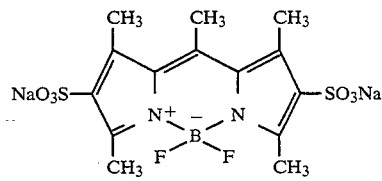

(Disodium salt of 4,4-difluoro-1,3,5,7,8-pentamethyl-4-bora-3a,4a-diaza-s-indacene-2,6-disulfonic acid monohydrate).

To prepare this compound, 0.5 g (0.002 moles) of 4,4-difluoro-1,3,5,7,8-pentamethyl-4-bora-3a,4a-diaza-s-indacene (prepared as described above in Example I) were combined with 20 ml of methylene chloride. The mixture of these materials (maintained at −10° C.) was combined with a solution of chlorosulfonic acid (0.24 ml, 0.004 moles) added drop-wise using a syringe. The mixture was stirred at −10° C. for approximately 0.5 hours and allowed to reach room temperature over a period of 1 hour. A suspended yellow solid was isolated by filtration, dissolved in 75 ml water and the solution was neutralized with sodium bicarbonate (0.30 grams). Sodium bicarbonate was continuously added thereafter until effervescence stopped. The aqueous solution was concentrated to approximately one-quarter its previous volume. Upon the addition of about 15 ml of ethanol, a yellow precipitate appeared which was isolated and dried in a desiccator under vacuum. The precipitate weighed approximately 0.66 grams, had a melting point of about 260° C., and represented the final product (the sodium salt of 4,4-difluoro-1,3,5,7,8-bora-3a,4a-diaza-s-indacene-2,6-disulfonic acid monohydrate-[$C_{14}H_{15}BF_2N_2O_6S_2Na_2 \cdot H_2O$]). Production of this product is shown in the following basic reaction:

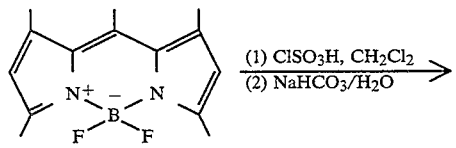

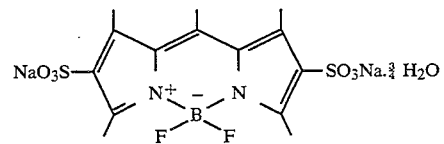

With respect to its use as a laser dye, the product had a lasing threshold of 10 kV with a lasing wavelength range of 545–585nm. This data was obtained using a 60 mg quantity of product dissolved in 230 ml of $H_2O$ in a 10 mm flashlamp dye laser manufactured by the Phas-R Company (Model D-1100).

As in Example I, tests were conducted on the product in Example II in order to determine its fluorescence in various solvents. Data showing a variety of different solvents combined with the product of Example II is presented below in Table II:

TABLE II

| Solvent | Solubility | Color of Solution | Fluorescence Room Light | Fluorescence UV |
|---|---|---|---|---|
| $CH_2Cl_2$ | Insoluble | | | |
| $CH_3CO_2C_2H_5$ | Insoluble | | | |
| $O(CH_2CH_2)_2O$ | Insoluble | | | |
| $CH_3C\equiv N$ | Very slightly soluble | yellowish green | yellowish green | yellowish green |
| $C_2H_5OH$ (95%) | Very slightly soluble | yellowish green | yellowish green | yellowish green |
| $(CF_3)_2CHOH$ | Insoluble | | | |
| $H_2O$ | Soluble | reddish orange | yellowish green | yellowish green |

In addition, a further test was conducted in order to determine the photostability of the product. Specifically, 2.0 mg of the product in a 100 ml round bottom flask was dissolved in 50 ml of $H_2O$. The solution was then irradiated by light from a 250 watt sun lamp placed approximately 8 inches from the flask. UV spectral data was recorded periodically as shown below in Table III.

TABLE III

| TIME (hours) | $\epsilon_{492}^{H2O}$ |
|---|---|
| 0 | 76,995.38 |
| 0.5 | 76,755.22 |
| 1.0 | 75,556.52 |
| 1.5 | 76,755.52 |
| 2.5 | 75,316.35 |
| 3.5 | 73,757.26 |
| 6.0 | 69,799.55 |
| 20.0 | 52,049.62 |
| 21.5 | 51,569.90 |
| 23.5 | 46,173.05 |
| 25.5 | 45,573.40 |
| 28.0 | 41,016.06 |
| 30.5 | 37,178.46 |
| 44.0 | 20,388.19 |
| 50.0 | 13,192.355 |
| 52.5 | 599.653 |

In addition to the two compounds described above in Examples I and II, the following is another preferred compound.

EXAMPLE III

The tricyclic structure of this Example has the following substitution pattern:

| | |
|---|---|
| $R_1 = C$ | $R_{12} = CH$ |
| $R_2 = C$ | $R_{13} = CH_3$ |
| $R_3 = C$ | $R_{14} = CH_2CH_3$ |
| $R_4 = C$ | $R_{15} = CH_3$ |
| $R_5 = C$ | $R_{15} = H$ |
| $R_5 = N$ | $R_{17} = CH_3$ |
| $R_7 = B$ | $R_{18} = CH_3$ |
| $R_8 = N$ | $R_{19} = H$ |
| $R_9 = C$ | $R_{29} = F$ |
| $R_{19} = C$ | $R_{21} = F$ |
| $R_{11} = C$ | |

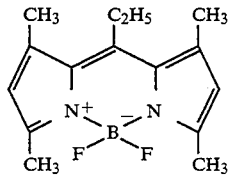

(4,4-difluoro-1,3,5,7-tetramethyl-8-ethyl-4-bora-3a,4a-diaza-s-indacene).

Table IV below summarizes the basic characteristics of the compounds of Examples I, II and III in comparison with a previously known compound (Rhodamine 590).

TABLE IV
Laser Characteristics of Pyrromethene-$BF_2$ Complexes Under Flashlamp Excitation

| cpd. | Example I | Example II | Example III | Rhodamine 590 |
|---|---|---|---|---|
| $\lambda L$ (nm) | 542 | 555 | 540 | 578 |
| $\Delta\lambda$ | 532–565 (33) | 545–585 (40) | 537–560 (23) | 565–612 (47) |
| Vth (kV) | 8–10 | 10 | 10 | 8 |
| $E_o$ (mJ) (V = 18 kV) | 85 | 80 | 90 | 100 |
| Life (kJ/L) | 50 (app.) | very long | * | 15 |
| Solvent | DMA/MeOH | DMA/MeOH | DMA/MeOH | DMA/MeOH |
| Conc(M) × $10^4$ | 1.5 | 2 | 2 | 0.5 |

*After 1000 S at 25 J, $E_o$~80 mJ

In addition, FIG. 1 shows the laser output E (in mJoule) as a function of input energy E (in Joule) of a $1.5 \times 10^{-4}$ molar solution of the compound of Example I (designated PMP-$BF_2$) dissolved in ethanol, a $2 \times 10^{-4}$ molar solution of Coumarin 545 dissolved in ethanol, a $2 \times 10^{-4}$ molar solution of Rhodamine 6G dissolved in ethanol, and a $2 \times 10^{-4}$ molar solution of the compound of Example II (designated PMP-$BF_2$-sulfonate) dissolved in ethanol.

EXAMPLE IV

Under synchronous pumping by a mode-locked Coherent Antares Nd:YAG laser, the dye 1,3,5,7,8-pentamethyl-2,6-diethylpyrromethene-$BF_2$ complex (PMDEP-$BF_2$gave twice the power output efficiency obtained from R-6G. PMDEP-$BF_2$ showed a photostability lifetime of 500 W-hrs.

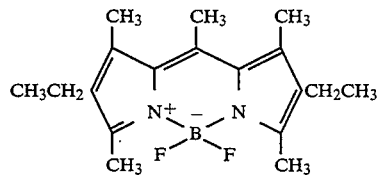

Similar results from tests in a Candela LFRDL 20 linear flashlamp dye laser showed the dye PMDEP-$BF_2$ to have 173% of the power efficiency of R-6G. In a similar manner the disodium salt of 1,3,5,7,8-pentamethylpyrromethene-2,6-disulfonic acid-$BF_2$ complex (PMPDS-$BF_2$) showed 145% of the power efficiency obtained from R-6G in a Candela LFDL-8 laser with flashlamp excitation, at a pulsewidth of 2 μsec, and a risetime 0.7 μsec.

In a continuous wave (CW) operation with an argon ion pump laser (5 watts all lines 457.9–514.5 nm) PMPDSBF-BF$_2$ gave 45% power efficiency and PMDEP-BF$_2$ gave 37%, whereas R-6G delivered a power output at 32%.

Under flashlamp excitation pulses the photostability in methanol of PMPDS-BF$_2$ (9000 pulses) was six times greater than that for R-6G (1500 pulses).

In a technological breakthrough P-BF$_2$ dyes homogeneously dispersed in an acrylic co-polymer were found to be superior "solid-state" lasers with the special feature of tunability characteristic of a laser dye. PMDEP-BF$_2$ ($10^{-4}$M) in a polymer matrix (5 parts methyl methacrylate and 1 part hydroxypropyl acrylate) gave a power efficiency of 88%. R-6G under similar treatment gave an unsatisfactory performance and was not measured; sulforhodamine-B gave a 37% efficiency. Similar tests showed other P-BF$_2$ dyes to rival and/or to surpass PMDEP-BF$_2$ in efficiency. The PMDEP-BF$_2$ and PMPDS were found to be particularly soluble in the polymer matrix.

The polymer matrix is disclosed in U.S. Pat. No. 5,136,005 which is incorporated by reference. Any laser dye of the present invention may be substituted for the dye in any of the examples of that incorporated patent. The matrix generally includes solid polymeric host laser rods prepared using bulk polymerization of acrylic acid ester comonomers. When the polymer is admixed with dyes capable of supporting laser oscillation and polymerized with a free radical initiator under mild thermal conditions, a solid product is produced having efficient lasing properties. Several dyes of the present invention have been found to have superior solubility in these polymer matrices, which in turn increases the efficiency of lasing action.

In a typical measurement of the P-BF$_2$ chromophore triplet-triplet (T—T) absorption for the dye PMPDS-BF$_2$ was barely detectable ($\epsilon_T \sim 3 \times 10^{-3}$) in the fluorescent spectral area.

These results made P-BF$_2$ dyes very suitable for performance in any situation where tunable lasing activity in the range 520–600 nm is called for.

LASER ACTIVITY

In the spectral region from 300 to 1300 nm, two groups of dye molecules have particularly been noted to have laser dye activity. The group of fused linear 6,6,6-tricyclic ring systems contains the dye rhodamine 6G (R-6G) 1.

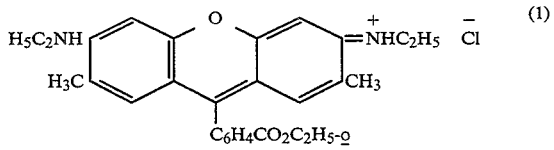

This laser dye had the highest power efficiency from flash lamp pumping known at the time of its discovery. In another group the cyanine dyes 2 were recognized for the ability of their luminophors in providing laser activity in the longer wavelengths, particularly >800 nm.

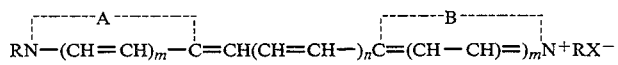

R is a substituent such as alkyl, X is an anion, m=0 or 1, and n=0–5.

A bathochromic shift of about 100 nm with each unit increase in n, the number of conjugated ethylenic units in the odd numbered carbon chain connecting two heterocyclic nuclei in the monobasic salt, brought about a distribution of absorption, fluorescence, and laser activity over a wide spectral region. Structures 3a, $\lambda_{las}$ 541 nm, and 3b, $\lambda_{las}$ 800 nm, are typical cyanine dyes.

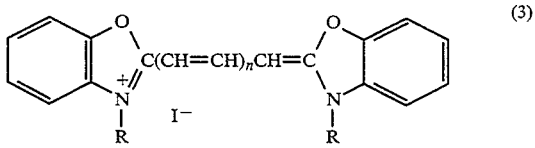

3a n = 1, R = C$_2$H$_5$
3b n = 3, R = CH$_3$

Tables I and II illustrate some of the compounds that will be discussed in the following sections

TABLE I

| 4, 5 | X | Y |
|---|---|---|
| a | CH$_3$ | H |
| b | CH$_3$ | CH$_3$ |
| c | CH$_3$ | CH$_2$CH$_3$ |
| d | CH$_3$ | (CH$_2$)$_2$CH$_3$ |
| e | CH$_3$ | (CH$_2$)$_3$CH$_3$ |
| f | CH$_3$ | CH(CH$_3$)$_2$ |
| g | CH$_3$ | C(CH$_3$)$_3$ |
| k | CH$_2$CH$_3$ | CH$_2$CH$_3$ |
| o | C$_6$H$_5$ | CH$_2$CH$_3$ |
| p | C$_6$H$_5$ | C$_6$H$_5$ |
| q | C$_6$H$_5$ | COCH$_3$ |

| 5 | X | Y |
|---|---|---|
| l | CH$_3$ | C$_6$H$_5$ |
| m | CH$_3$ | NHCOCH$_3$ |
| n | OCH$_3$ | CH$_3$ |

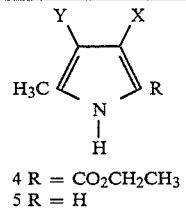

4 R = CO$_2$CH$_2$CH$_3$
5 R = H

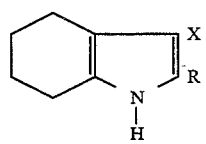

4i X = CH$_3$, R = CO$_2$C$_2$H$_5$
5h X = R = H
5i X = CH$_3$, R = H

TABLE I-continued

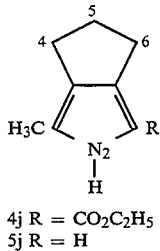

4j R = CO₂C₂H₅
5j R = H

TABLE II

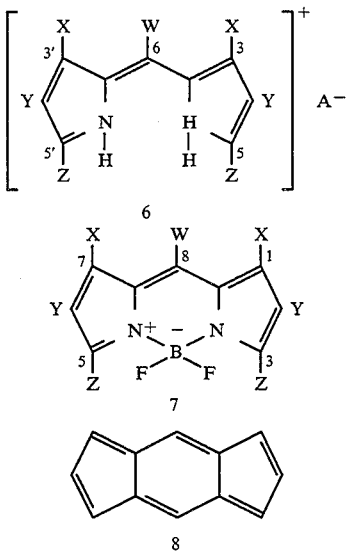

| 6, 7 | W | X | Y | Z | A |
|---|---|---|---|---|---|
| a | CH₃ | CH₃ | H | CH₃ | Cl |
| b | CH₃ | CH₃ | CH₃ | CH₃ | Cl |
| c | CH₃ | CH₃ | CH₂CH₃ | CH₃ | Cl |
| d | CH₃ | CH₃ | (CH₂)₂CH₃ | CH₃ | Cl |
| e | CH₃ | CH₃ | (CH₂)₃CH₃ | CH₃ | Cl |
| f | CH₃ | CH₃ | CH(CH₃)₂ | CH₃ | Cl |
| g | CH₃ | CH₃ | C(CH₃)₃ | CH₃ | Cl |
| h | CH₃ | H | (CH₂)₄ | | Cl |
| i | CH₃ | CH₃ | (CH₂)₄ | | Cl |
| j | CH₃ | (CH₂)₃ | | CH₃ | Cl |
| k | CH₃ | CH₂CH₃ | CH₂CH₃ | CH₃ | Cl |
| l | CH₃ | CH₃ | C₆H₅ | CH₃ | Cl |
| m | CH₃ | CH₃ | NHCOCH₃ | CH₃ | Cl |
| n | CH₃ | OCH₃ | CH₃ | CH₃ | Cl |
| o | CH₂CH₃ | CH₃ | CH₂CH₃ | CH₃ | Cl |
| p | CH(CH₃)₂ | CH₃ | CH₂CH₃ | CH₃ | Cl |
| q | c-C₆H₁₁ | CH₃ | CH₂CH₃ | CH₃ | Cl |
| r | CH₂OCOCH₃ | CH₃ | CH₂CH₃ | CH₃ | Cl |
| s | p-(CH₃)₂NC₆H₅ | CH₃ | CH₂CH₃ | CH₃ | Cl |
| t | p-CH₃OC₆H₅ | CH₃ | H | CH₃ | Cl |
| u | H | C₆H₅ | CH₂CH₃ | CH₃ | Br |
| v | H | C₆H₅ | C₆H₅ | CH₃ | Br |
| w | H | C₆H₅ | H | CH₃ | Br |
| x | H | CH₃ | C(CH₃)₃ | CH₃ | Br |
| y | H | CH₂CH₃ | CH₂CH₃ | CH₃ | Br |
| z | H | CH₃ | CH₃ | CH₃ | Br |
| aa | CN | CH₃ | CO₂CH₂CH₃ | CH₃ | Br |
| bb | CN | CH₃ | CH₂CH₃ | CH₃ | Br |

The invention includes any combination of the compounds in Table II, or any subcombinations thereof.

Compounds 7h and 7i each have a four carbon bridge —(CH₂)₄— as substituents Y and Z. Compound 7j has a three carbon bridge —(CH₂)₃— as substituents X and Y, that forms a five membered ring (see Example VII).

The P-BF₂ molecules 7 uniquely blended the structural features of a cyanine dye 2, n=3, and a planar fused tricyclic ring system and introduced laser dyes with a linear 5,6,5-tricyclic ring system. The parent linear 5,6,5-tricyclic antiaromatic (4n π e) hydrocarbon, s-indacene C₁₂H₈ was a red solid but was not described as fluorescent. In contrast the parent 6,6,6-tricyclic aromatic (4n+2π e) hydrocarbon, anthracene C₁₄H₁₀, showed λ$_f$ 400 nm.

Although pyrromethene salts also met the structural requirement of a cyanine dye with n=3, such salts were weakly fluorescent. For example, 3,3′,5 5′-tetramethyl-4,4′diethylpyrromethene hydrobromide 9 (Table III) showed Φ$_f$ 4.3×10⁻⁴.

TABLE III

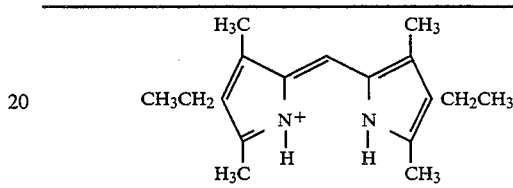

Br⁻
9

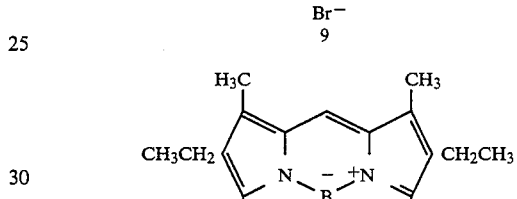

10 R = CH₂CH₃
11 R = F

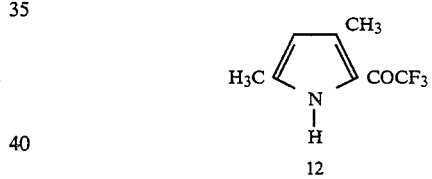

12

Conversion to boron complexes, such as 1,3,5,7-tetramethyl-2,6-diethylpyrromethene-B(CH₂CH₃)₂ complex 10 (Φ$_f$ 0.31) and the corresponding BF₂ complex 11 (Φ$_f$ 0.81) raised the fluorescence quantum yield by a thousand fold. In addition laser activity 550 to 570 nm became a characteristic property of P-BF₂ 7. This property qualified P-BF₂ compounds as bridged cyanine dyes, n=3, with the particular feature of a hypsochromic shift of over 200 nm from λ$_{las}$ 800 nm observed for a linear cyanine dye 3b, n=3.

A general synthesis scheme of the compounds in Table II is described in the following section, with reference to the compounds in Table I.

A Knorr cyclization between ethyl a—aminoacetoacetate (prepared in situ) and a 3-alkyl-2,4-pentandione was selected for the preparation of ethyl alkylpyrrole-2 carboxylate derivatives 4b–f, i. Ethyl 3,5-dimethyl-4-tertbutylpyrrole-2-carboxylate 4g was prepared from ethyl 3,5-dimethylpyrrole-2-carboxylate 4a in an alkylation with tert-butyl acetate. In a modification of a Knoevenagel condensation of ethyl N-(3-oxo-1-alkenyl)aminoacetates to ethylpyrrole-2-carboxylates ethyl 3-methyl-2,4,-5,6-tetrahydrocyclopenta[c]pyrrolecarboxylate 4j was obtained by a base catalyzed cyclization of an unisolated enamine 13 (Table IV), in turn obtained from a condensation between glycine ethyl ester and α-acetylcyclopentanone.

TABLE IV

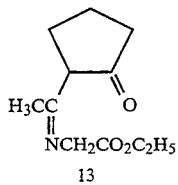

13

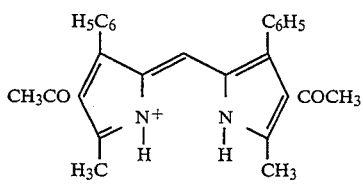

14

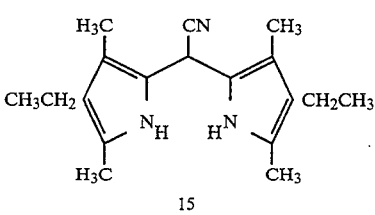

15

Conversion of α-pyrrolecarboxylate esters to α-unsubstituted pyrroles by treatment with phosphoric acid provided a convenient preparation of pyrrole 5b and was extended to 3-n-propyl, 3-n-butyl, and 3-isopropyl derivatives 5d–f of 2,4-dimethylpyrrole 5a. A similar conversion afforded 3-methyl-4,5,6,7-tetrahydroindole 5i from its 2-carboxylate ester derivative 4i. Unsuccessful attempts to extend the method to the preparation of 2,4-dimethyl-3-tert-butylpyrrole 5g led instead to the replacement of both the carboethoxy and tert-butyl groups with hydrogen to give 2,4-dimethylpyrrole 5a. The pyrroles 5g, j, k were obtained from ethyl 3',5'-dimethyl-4-tert-butylpyrrole-2-carboxylate 4g, ethyl 3-methyl-2,4,5,6-tetrahydrocyclopenta[c]pyrrolecarboxylate 4j, and ethyl 3,4-diethyl-5-methylpyrrole-2-carboxylate 4k by saponification with potassium hydroxide followed by decarboxylation of the free acids in ethanolamine at 180° C.

Synthesis of Pyrromethene-BF₂ Complexes (P-BF₂)

Treatment with an acyl chloride converted pyrroles 5 (Table I) to P-BF₂ 7 (Table II) via unstable and generally unisolated pyrromethene hydrochlorides 6. Kryptopyrrole 5c and acetyl chloride gave the isolated but unstable 3,5,3',5',6-pentamethyl-2,6-diethylpyrromethene hydrochloride 6c. It was subsequently determined that conversion of the unstable intermediate 6c without isolation to PMDEP-BF₂ 7c by treatment with boron trifluoride etherate was recommended and became the basis for a general procedure for conversions of other pyrroles to P-BF₂. Derivatives of 2,4-dimethylpyrrole with 3-substituents (n-propyl 5d, n-butyl 5e, isopropyl 5f, tert-butyl 5g, phenyl 5l, and acetamido 5m) gave the corresponding 2,6-disubstituted derivatives 7d–g, l, m of 1,3,5,7,8-pentamethylpyrromethene-BF₂ complex (PMP-BF₂) 7a. Similar treatment with acetyl chloride converted tetrahydroindole 5h, 3-methyltetrahydroindole 5i, 3-methyl-2,4,5,6-tetrahydrocyclopenta[c]pyrrole 5j, and 3,4-diethyl-5-methylpyrrole 5k to 2,3,6,7-bistetramethylene-8-methylpyrromethene-BF₂ complex 7h, its 1,7-dimethyl derivative 7i, 1,2,6,7-bistrimethylene-3,5,8-trimethylpyrromethene-BF₂ complex 7j, and 1,2,6,7-tetraethyl-3,5,8-trimethylpyrromethene BF₂ complex 7k and converted 2,3-dimethyl-4-methoxypyrrole 5n to 1,7-dimethoxy-2,3,5,6,8-pentamethylpyrromethene-BF₂ complex 7n.

Kryptopyrrole 5c condensed with propionyl chloride, isobutyryl chloride, cyclohexanecarbonyl chloride, acetoxyacetyl chloride, and p-dimethylaminobenzoyl chloride to produce the 8-ethyl, 8-isopropyl, 8-cyclohexyl, 8-acetoxymethyl, and 8-dimethylaminophenyl derivatives 7o–s of 1,3,5,7-tetramethyl-2,6-diethylpyrromethene-BF₂ complex. A straightforward extension of the procedure was found in the reaction between 2,4-dimethylpyrrole 5a and p-anisoyl chloride to give 1,3,5,7-tetramethyl-8-p-methoxyphenylpyrromethene-BF₂ complex 7t via the intermediacy of the otherwise uncharacterized pyrromethene hydrochloride 6t. Attempts to convert 2-trifluoroacetyl-3,5-dimethylpyrrole 12 to a derivative of 8-trifluoromethylpyrromethene-BF₂ complex were unsuccessful.

Treatment with hydrobromic acid in formic acid brought about the conversion of α-pyrrolecarboxylate esters 4 to pyrromethene hydrobromides 6 via the presumed intermediacy of α-unsubstituted pyrroles 5 followed by condensations with formyl derivatives formed in situ. Thus the esters 4k, o, p afforded the pyrromethene salts 6y, 6u, and 6v respectively. Straightforward treatment with boron trifluoride etherate converted these crude pyrromethene hydrobromides to 1,2,6,7-tetraethyl-3,5-dimethylpyrromethene-BF₂ complex 7y, and the 1,7-diphenyl-2,6-diethyl-3,5 dimethyl and 1,2,6,7-tetraphenyl-3,5-dimethylpyrromethene-BF₂ derivatives 7u, v.

Similar treatment converted 3,3'-diphenyl-4,4'-diacetyl-5,5'-dimethylpyrromethene hydrobromide 14 (from ethyl 3-phenyl-4-acetyl-5-methylpyrrole-2 carboxylate 4q) after an initial deacetylation to 1,7-diphenyl-3,5-dimethylpyrromethene-BF₂ complex 7w. An assumed unisolated pyrromethene hydrobromide intermediate 6x from the pyrrolecarboxylate ester 4g was converted to 1,3,5,7-tetramethyl-2,6-di-tert-butylpyrromethene-BF₂ complex 7x.

Addition of hydrogen cyanide to the pyrromethene hydrobromide 9 presumably brought about the formation of 3,5,3',5'-tetramethyl-4,4'-diethyl-6-cyanopyrromethane 15. Dehydrogenation by bromine followed by treatment with boron trifluoride etherate converted the pyrromethane 15 to 1,3,5,7-tetramethyl-2,6-diethyl-8-cyanopyrromethene-BF₂ complex 7bb via the corresponding pyrromethene hydrobromide 6bb.

LASER ACTIVITY

Variation in similar pairs of 2,6-dialkyl substituents in derivatives 7b–g of PMP-BF₂ 7a was carried out to demonstrate which dyes were competitive with PMDFP-BF₂ 7c in laser activity. As the pairs of similar 2,6-disubstituents changed from hydrogen to methyl, ethyl, n-propyl, n-butyl, and isopropyl in dyes 7a–f the electronic absorption shifted from $\lambda_{max}$ 493 nm to 517±1 nm with a nearly constant log ε 4.8+0.1. A significantly larger bathochromic shift led to $\lambda_{max}$ 525, log ε 4.83, for the 2,6-di-tert-butyl derivative 7g, Table 1.

Laser activity $\lambda_{las}$ was previously reported for PMP-BF₂ 7a at 542 nm and for PMDEP-BF₂ 7c at 570 nm in Shah et al., Heteratom. Chem. 1:389, 1990. Similar activity was found in the 2,6-dimethyl, 2,6 di-n-propyl, 2,6-di-n-butyl, and 2,6-diisopropyl derivatives 7b, d–f at 573, 578, 580, and 577 nm and in the 2,6-di-tert-butyl derivative 7g at 597 nm. In partial fulfillment of the 5 factors contributing to laser activity each of these seven dyes showed high extinction coefficients log ε 4.8 to 4.9 and high fluorescence quantum yields $\Phi_f$ 0.67 to 0.99. PMP-BF$_2$ 7a, PMDEP-BF$_2$ 7c, and the 2,6-di-n-butyl derivative 7e were superior to the other four 2,6-dialkyl derivatives in laser activity RE (relative efficiency in power output where RE 100 is arbitrarily assigned to rhodamine-6G).

The data revealed an alternation in RE as the 2,6-di-n-alkyl substituents contained an odd number of carbon atoms 7b, d (RE 65, 85) or zero and an even number of carbon atoms 7a, c, e, RE≧100, Table VI. Although the bistetramethylene dyes 7h, i and the bistrimethylene dye 7j gave nearly identical $\lambda_{max}$ with high extinction coefficients log ε>4.8 and shared strong fluorescence $\Phi_f$≧0.8 they differed significantly in laser activity with RE≧75 for the bistetramethylene dyes and RE 20 for the bistrimethylene dye, Table VI. The structure for the dye 7j was confirmed by an X-ray crystallographic analysis to have chromophore planarity with negligible strain. Hence compounds 7 are preferred wherein Y is n-alkyl or t-alkyl containing an even number of carbons, especially 2 or 4 carbons.

Alkyl and other group substituent effects at the 8-position in 1,3,5,7-tetramethyl-2,6-dialkylpyrromethene-BF$_2$ complex structures were examined. In comparison with peralkylated structures (7b, g, k) corresponding examples lacking a substituent at the 8-position (7z, x, y) showed a slight bathochromic shift in absorption, an erratic effect on fluorescence, and a marked decrease in laser activity RE, Table VI. Presumably non planarity for 1,3,5,7-tetramethyl-2,6-diethyl-8-isopropylpyrromethene-BF$_2$ complex 7p was brought about by a steric interaction between the isopropyl group and the 1,7-dimethyl substituents and led to the large reduction in fluorescence and the loss of laser activity. A similar steric effect was introduced by the replacement of the 8-ethyl substituent in 1,3,5,7-tetramethyl-2,6,8-triethylpyrromethene-BF$_2$ complex 7o $\Phi$0.84 with 8-cyclohexyl to bring about reduction in the fluorescence quantum yield to $\Phi$0.23 and no laser activity for the dye 1,3,5,7-tetramethyl-2,6 diethyl-8-cyclohexylpyrromethene-BF$_2$ complex 7q. Insofar as laser dyes with cyano substituents are unusual, the laser activity in diethyl 1,3,5,7-tetramethyl-8-cyanopyrromethene-2,6-dicarboxylate-BF$_2$ complex 7aa and 1,3,5,7-tetramethyl-2,6-diethyl-8-cyanopyrromethene-BF$_2$ complex 7bb presented exceptional interest. Four cyano substituted laser dyes were listed by Maeda in *Laser Dyes*, Academic Press, Tokyo, Japan, 1984, pp. 19–21.

Pairs of similar functional group (polar) substituents in the 2,6-positions of P-BF$_2$ dyes brought about erratic results in RE. Fluorescence and laser activity were reduced in a P-BF$_2$ dye by a nitro substituent and quenched by a bromo substituent. Metal and ammonium salts of 1,3,5,7,8-pentamethylpyrromethene-2,6-disulfonic acid-BF$_2$ complex 16 (Table V) were exceptionally powerful dyes with RE 95 but the sodium salt of 1,3,5,7-tetramethyl-8-ethylpyrromethene-2,6-disulfonic acid-BF$_2$ complex 17 showed RE 50. Low values were also obtained for the disulfonate ester 18 RE 35, the dicarboxylate ester 19 RE 50, the 2,6-diacetamido derivative 7m RE 5 and the 2,6-diphenyl derivative 7l RE 20. The singular example of 1,7-dimethoxy-2,3,5,6,8-pentamethylpyrromethene-BF$_2$ complex 7n RE 30 suggested that laser activity was diminished by electron donating substituents at the 1,7-positions. Low lasing activity resulted from the introduction of phenyl substituents in the 1- and 2-positions in dyes 7l, 7u, and 7w and the absence of lasing activity was noted for 1,2,6,7-tetraphenyl-3,5-dimethylpyrromethene-BF$_2$ complex 7v.

TABLE V

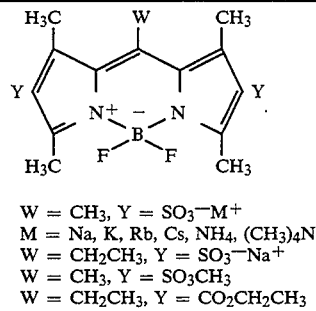

| | |
|---|---|
| 16 | W = CH$_3$, Y = SO$_3^-$M$^+$ |
| | M = Na, K, Rb, Cs, NH$_4$, (CH$_3$)$_4$N |
| 17 | W = CH$_2$CH$_3$, Y = SO$_3^-$Na$^+$ |
| 18 | W = CH$_3$, Y = SO$_3$CH$_3$ |
| 19 | W = CH$_2$CH$_3$, Y = CO$_2$CH$_2$CH$_3$ |

Spectroscopic Measurements

Instruments for spectroscopic measurements included: Perkin-Elmer 1600 FTIR, Varian Gernini 300 NMR, Hewlett-Packard 5985 (70 eV) GC-MS, Cary 17 (UV), and Perkin-Elmer LS-5B Luminescence spectrometer. A dye laser was constructed and operated in the non-flowing (static) mode and had no tuning capability. The dye cell (2.5 mm diameter, 50 mm long) had an elliptical cavity configuration of small eccentricity. The flashlamp EG & G model FX 139C-2 produced a pulse that had a rise time of 200 ns, half-width length of 600 ns, and input energy of 2 J at 6.32 kV, 5 J at 10.00 kV, 7.2 J at 12.00 kV, and 10 J at 14.14 kV. Laser energy outputs were measured with an accuracy of ±5% by a Scientech 365 power and energy meter.

Light absorption, luminescence, and laser activity properties for the dyes 7 are described in Table VI. Each recorded UV absorption was restricted to the highest wave length. Fluorescence quantum yields of the dyes were determined for ethanol solutions with excitation at 450 and 460 nm by reference to acridine orange, $\Phi$0.46, in ethanol; for the dye 7p the reference was R-6G, <P 0.90. Table VII lists yield, mp, $^1$H NMR, and elemental analysis for the laser dyes 7. Melting points were obtained from a Mel-Temp II device and were uncorrected. The solvent for $^1$H NMR spectra was chloroform-d with tetramethylsilane as an internal standard. Elemental analyses were obtained from Midwest Micro Lab, Indianapolis, Ind. and Galbraith Laboratories, Inc., Knoxville, Tenn. Solvents were removed by rotary evaporation under reduced pressure unless indicated otherwise. Column chromatography was performed on silica gel. Molecular weights were confirmed by EI-MS for the pyrrole 4j 193 and for laser dyes 7d 346, 7e 374, 7g 374, 7i 342, 7j 314 and 7x 360. IR absorption data satisfactorily supported structure assignments for the laser dyes 7.

TABLE VI

| | Pyrromethene — BF$_2$ Laser Dyes 7 | | | | | |
|---|---|---|---|---|---|---|
| 7 | $\lambda_{max}^a$ (nm) | log ε | $\lambda_f^b$ (nm) | $\Phi_f$ | $\lambda_{las}^b$ (nm) | RE$^c$ |
| a$^d$ | 493 | 4.90 | 519 | 0.99 | 542 | 100 |
| b$^d$ | 518 | 4.67 | 546 | 0.70 | 573 | 65 |
| c$^d$ | 517 | 4.81 | 546 | 0.83 | 570 | 110 |

TABLE VI-continued

Pyrromethene — BF$_2$ Laser Dyes 7

| 7 | $\lambda_{max}^a$ (nm) | log ε | $\lambda_f^b$ (nm) | $\Phi_f$ | $\lambda_{las}^b$ (nm) | RE$^c$ |
|---|---|---|---|---|---|---|
| d | 517 | 4.89 | 549 | 0.99 | 578 | 85 |
| e | 518 | 4.92 | 550 | 0.90 | 580 | 100 |
| f | 516 | 4.85 | 548 | 0.67 | 577 | 45 |
| g | 525 | 4.83 | 567 | 0.77 | 597 | 50 |
| h | 535 | 4.93 | 560 | 0.84 | 589 | 75 |
| i | 522 | 4.91 | 552 | 0.80 | 582 | 90 |
| j | 512 | 4.82 | 535 | 0.81 | 560 | 20 |
| k | 521 | 4.89 | 554 | 0.75 | 582 | 75 |
| l | 519 | 4.90 | 559 | 0.43 | 582 | 20 |
| m | 498$^e$ | 4.63 | 542$^f$ | 0.17 | 566$^f$ | 5 |
| n | 485 | 4.85 | 522 | 0.84 | 540 | 30 |
| o | 520 | 4.92 | 546 | 0.84 | 571 | 75 |
| p | 527 | 4.84 | 562 | 0.07$^g$ | h | — |
| q | 516 | 4.81 | 526 | 0.23 | h | — |
| r | 543 | 4.89 | 575 | 0.74 | 605 | 30 |
| s | 519 | 4.95 | 575 | 0.04 | h | — |
| t | 497 | 4.86 | 521 | 0.63 | 547 | 50 |
| u | 540 | 5.00 | 564 | 0.60 | 582 | 10 |
| v | 552 | 4.91 | 590 | 0.69 | h | — |
| w | 521 | 4.92 | 551 | 0.61 | 580 | 5 |
| x | 527 | 4.93 | 554 | 0.84 | 580 | 30 |
| y | 529 | 4.89 | 554 | 0.70 | 580 | 40 |
| z | 528 | 4.84 | 552 | 0.56 | 570 | 30 |
| aa | 556$^i$ | 4.98 | 589$^i$ | 0.82 | 617$^i$ | 55 |
| bb | 580$^i$ | 4.72 | 620$^i$ | 0.55 | 670$^{i,j}$ | $^k$ |

[a] $5 \times 10^{-6}$M in ethanol except where noted otherwise.
[b] $2 \times 10^{-4}$M in ethanol except where noted otherwise.
[c] Relative Efficiency 100 assigned to R - 6G.
[d] Ref [2].
[e] $5 \times 10^{-6}$M in trifluoroethanol.
[f] $2 \times 10^{-4}$M in trifluoroethanol.
[g] With reference to R - 6G Φ 0.90 (K. H. Drexhage, J. Res. Nat. Bur. Std., 1976, 80A, 421).
[h] No laser activity detected.
[i] $2 \times 10^{-4}$M in p - dioxan.
[j] Obtained from a Phase - R DL - 1100 dye laser with DL - 5Y coaxial flashlamp.
[k] RE not determined.

TABLE VII

Pyrromethene-BF$_2$ Laser Dyes 7

| No. | Yield % | mp °C. | $^1$H NMR(CDCl$_3$) δ | Formula Calculated % Found % |
|---|---|---|---|---|
| 7d | 21 | 193–194 | 2.57(s, 3H), 2.46(s, 6H), 2.33(t, 4H), 2.29(s, 6H), 1.42(m, 4H), 0.91(t, 6H) | C$_{20}$H$_{29}$N$_2$BF$_2$<br>C, 68.86; H, 8.32; N, 8.03<br>C, 69.46; H, 8.25; N, 8.04 |
| 7e | 18 | 185–186 | 2.58(s, 3H), 2.47(s, 6H), 2.35(t, 4H), 2.30(s, 6H), 1.35(m, 8H), 0.91(t, 6H) | C$_{22}$H$_{33}$N$_2$BF$_2$<br>C, 70.62; H, 8.83; N, 7.49<br>C, 69.91; H, 8.81; N, 7.39 |
| 7f | 15 | 186 dec | 2.5(s, 3H), 2.3(s, 6H) 2.1(s, 6H), 1.9–2.0(m, 2H) 0.9–1.0(d, 12H) | C$_{20}$H$_{29}$N$_2$BF$_2$<br>C, 69.36; H, 8.38; N, 8.09; F, 10.98<br>C, 69.40; H, 8.29; N, 8.13; F, 11.10 |
| 7g | 15 | 246–247 | 2.67(s, 6H), 2.59(s, 3H) 2.46(s, 6H), 1.39(s, 18H) | C$_{22}$H$_{33}$N$_2$BF$_2$<br>C, 70.62; H, 8.83; N, 7.49<br>C, 71.09; H, 9.01; N, 7.34 |
| 7h | 19 | 191–192 | 6.8(s, 2H), 3.03(s, 3H) 2.5(t, 8H), 1.77(t, 8H) | C$_{18}$H$_{21}$N$_2$BF$_2$<br>C, 68.78; H, 6.68; N, 8.91<br>C, 68.57; H, 6.72; N, 8.75 |
| 7i | 32 | 265–267 | 2.96(t, 4H), 2.56(s, 3H) 2.40(t, 4H), 2.26(s, 6H) 1.76(m, 8H) | C$_{20}$H$_{25}$N$_2$BF$_2$<br>C, 70.21; H, 7.31; N, 8.19<br>C, 70.99; H, 7.49; N, 8.26 |
| 7j | 14 | 268–269 dec | 2.68(t, 4H), 2.53(t, 4H), 2.46(s, 6H), 2.40(m, 4H), 2.34(s, 3H) | C$_{18}$H$_{21}$N$_2$BF$_2$<br>C, 68.83; H, 6.69; N, 8.92<br>C, 68.99; H, 6.72; N, 8.76 |
| 7k | 40 | 120 | 2.74–2.79(q, 4H), 2.68(s, 3H), 2.49(s, 6H), 2.35–2.40 (q, 4H), 1.16–1.21(t, 6H), 1.04–1.09(t, 6H) | C$_{20}$H$_{29}$N$_2$BF$_2$<br>C, 69.36; H, 8.38; N, 8.09; F, 10.98<br>C, 69.09; H, 8.43; N, 8.05; F, 10.74 |
| 7l | 45 | 234–236 dec | 7.2–7.4(s, 10H), 2.6(s, 3H) 2.45(s, 6H), 2.3(s, 6H) | C$_{26}$H$_{25}$N$_2$BF$_2$<br>C, 75.54; H, 6.05; N, 6.77; F, 9.20<br>C, 75.78; H, 6.34; N, 6.64; F, 9.41 |
| 7m | 19 | 340–343 dec | 9.27(s, NH), 2.66(s, 3H) 2.29(s, 6H), 2.25(s, 6H) 2.06(s, 6H) | C$_{18}$H$_{23}$N$_4$O$_2$BF$_2$<br>C, 57.29; H, 6.36; N, 14.85<br>C, 57.06; H, 6.18; N, 14.36 |
| 7n | 31 | 210–211 | 3.9(s, 6H), 2.65(s, 3H) 2.47(s, 6H), 2.0(s, 6H) | C$_{16}$H$_{21}$N$_2$O$_2$BF$_2$<br>C, 59.62; H, 6.52; N, 8.69<br>C, 59.71; H, 6.68; N, 8.77 |
| 7o | 60 | 150–152 | 3.07(q, 2H), 2.52(s, 6H) 2.42(q, 4H), 2.38(s, 6H) 1.34(t, 3H), 1.07(t, 6H) | C$_{19}$H$_{27}$N$_2$BF$_2$<br>C, 68.69; H, 8.19; N, 8.43<br>C, 68.80; H, 8.14; N, 8.40 |
| 7p | 29 | 127–128 | 2.5(m, 17H), 1.5(d, 6H), 1.07(t, 6H) | C$_{20}$H$_{29}$N$_2$BF$_2$<br>C, 69.36; H, 8.38; N, 8.09<br>C, 69.37; H, 8.44; N, 8.10 |
| 7q | 45 | 185 dec | 2.40–2.60(m, 16H), 1.35–2.30(m, 11H), 1.03–1.08(t, 6H) | C$_{23}$H$_{33}$N$_2$BF$_2$<br>C, 71.50; H, 8.54; N, 7.25<br>C, 71.86; H, 8.57; N, 7.42 |
| 7r | 18 | 181–182 | 5.3(s, 2H), 2.5(m, 19H), 1.05(t, 6H) | C$_{20}$H$_{27}$N$_2$O$_2$BF$_2$<br>C, 63.82; H, 7.18; N, 7.44<br>C, 63.69; H, 7.20; N, 7.41 |
| 7s | 32 | 330–332 dec | 6.7–7.1(m, 4H), 3.1(s, 6H) 2.5(s, 6H), 2.2–2.3(q, 4H) 1.3(s, 6H), 1.1(t, 6H) | C$_{25}$H$_{32}$N$_3$BF$_2$<br>C, 70.92; H, 7.56; N, 9.92; F, 8.98<br>C, 71.09; H, 7.82; N, 9.55; F, 8.49 |
| 7t | 42 | 212–214 dec | 7.1–7.3(m, 4H), 6.1(s, 2H) 3.8(s, 3H), 2.3(s, 6H) 1.3(s, 6H) | C$_{20}$H$_{21}$N$_2$OBF$_2$<br>C, 67.80; H, 5.93; N, 7.91; F, 10.74<br>C, 67.75; H, 6.01; N, 7.88; F, 10.75 |
| 7u | 52 | 230–232 dec | 7.33(s, 10H), 6.3(s, 1H) | C$_{27}$H$_{27}$N$_2$BF$_2$ |

TABLE VII-continued

Pyrromethene-BF$_2$ Laser Dyes 7

| No. | Yield % | mp °C. | $^1$H NMR(CDCl$_3$) δ | Formula Calculated % Found % |
|---|---|---|---|---|
| 7v | 42 | 308–310 dec | 2.44–2.65(m, 10H), 1.04(t, 6H) 7.1–7.4(m, 21H), 2.6(s, 6H) | C, 75.73; H, 6.31; N, 6.54; F, 8.88 C, 75.65; H, 6.37; N, 6.28; F, 8.76 C$_{35}$H$_{27}$N$_2$BF$_2$ C, 80.18; H, 5.15; N, 5.34; F, 7.25 C, 79.85; H, 5.24; N, 5.26; F, 7.36 |
| 7w | 40 | 225 dec | 7.2–7.5(m, 12H), 6.39(s, 1H) 2.66(s, 6H) | C$_{23}$H$_{19}$N$_2$BF$_2$ C, 74.19; H, 5.10; N, 7.52; F, 10.21 C, 74.21; H, 5.10; N, 7.38; F, 9.93 |
| 7x | 9 | 235–236 | 6.98(s, 1H), 2.66(s, 6H) 2.29(s, 6H), 1.36(s, 18H) | C$_{21}$H$_{31}$N$_2$BF$_2$ C, 70.00; H, 8.61; N, 7.77 C, 69.51; H, 8.78; N, 7.45 |
| 7y | 57 | 116–117 | 6.93(s, 1H), 2.5(m, 14H) 1.1(m, 12H) | C$_{19}$H$_{27}$N$_2$BF$_2$ C, 68.67; H, 8.13; N, 8.43 C, 68.70; H, 8.21; N, 8.34 |
| 7z | 52 | 275 dec | 6.94(s, 1H), 2.47(s, 6H) 2.14(s, 6H), 1.97(s, 6H) | C$_{15}$H$_{19}$N$_2$BF$_2$ C, 65.45; H, 6.90; N, 10.18; F, 13.81 C, 65.26; H, 6.85; N, 10.16; F, 13.90 |
| 7bb | 9 | 155–156 | 2.4(m, 16H), 1.05(t, 6H) | C$_{18}$H$_{22}$N$_3$BF$_2$ C, 65.65; H, 6.68; N, 12.76 C, 65.46; H, 6.63; N, 12.63 |

Other Materials

Commercially available pyrroles included ethyl 3,5-dimethylpyrrole-2-carboxylate 4a, ethyl 3,4-diethyl-5-methylpyrrole-2-carboxylate 4k, 2,4-dimethyl 3-ethylpyrrole 5c (kryptopyrrole), and 4,5,6,7-tetrahydroindole 5h.

The following pyrroles and pyrromethene derivatives were prepared by the methods cited: ethyl 3,5-dimethyl-4-ethylpyrrole-2-carboxylate 4c (Kleinspehn, J. Amer. Chem. Soc. 77:1546, 1955), ethyl 3,4-diethyl-5-methylpyrrole-2-carboxylate 4k (Wang and Chang, Synthesis, p. 548, 1979), ethyl 3-phenyl-4-ethyl-5-methylpyrrole-2-carboxylate 4o (Ogoshi et al., Tetrahedron Lett. 24:929, 1983); Guy and Jones, Aust. J. Chem. 19:1871, 1966), ethyl 3,4-diphenyl-5-methylpyrrole-2-carboxylate 4p (Guy and Jones, 1966), ethyl 3-phenyl-4-acetyl-5-methylpyrrole-2-carboxylate 4q (Guy and Jones, 1966), 2,4-dimethylpyrrole 5a (Treibs and Schulze, Leibigs Ann. Chem. 739:222, 225, 1970), 2,4-dimethyl-3-phenylpyrrole, 51 (Guy and Jones, 1966), 3-acetamido-2,4-dimethylpyrrole 5m (Zavyalov et al., Izv. Akad. Nauk. Ser. Khim. 1906, 1973), 3-methoxy-4,5-dimethylpyrrole 5n (Bauer, Leibigs, Ann. Chem. 736:1, 1970), 1,2,3,5,6,7-hexamethylpyrromethene-BF$_2$ complex 7z (Vos de Wael, Recl. Trav. Chim. Pay-Bas 96:306, 1977), diethyl 1,3,5,7-tetramethyl-8-cyanopyrromethene-2,6-dicarboxylate-BF$_2$ complex 7aa (Treibs and Kreuzer, Liebigs Ann Chem 718:208, 1968), and 3,5,3',5'-tetramethyl-4,4'-diethylpyrromethene hydrobromide 9 (Johnson et al., J. Chem. Soc. 3416, 1959).

3-n-Propyl-2,4,-pentanedione. A mixture of iodopropane (317 g, 1.87 mol), 2,4-pentanedione (146 g, 1.51 mol) and anhydrous potassium carbonate (200 g) in dry acetone (300 ml) was heated at 60° C. for 20 h, cooled, combined with petroleum ether (300 ml), and filtered. The filtrate was washed with a mixture (1:1, 200 ml) of petroleum ether and acetone. Solvent removal left 3-n-propyl-2,4-pentanedione as a light yellow oil, 53 g (25%), bp 195° C. (lit. bp 73° C./11 mm). In a similar procedure (a) iodobutane and 2,4-pentanedione gave 3-n-butyl-2,4-pentanedione as a light yellow oil, 28%, bp 208° C. (lit. bp 104°–106° C./20 mm) and (b) isopropyl iodide and 2,4-pentanedione gave 3-isopropyl-2,4-pentanedione as a light yellow oil, 40%, bp 182° C. (lit. bp 94° C./45 mm).

Ethyl 3,5-dimethyl-4-n-propylpyrrole-2-carboxylate 4d. A solution of sodium nitrite (28.2 g, 0.41 mol) in water (100 ml) was added to a stirred cold solution of ethyl acetoacetate (49.4 g, 0.38 mol) in acetic acid as the temperature was held below 15° C. After the solution was stirred and stored overnight at 25° C., 3-n-propyl-2,4-pentanedione (53.7 g, 0.38 mol) and zinc (53 g) were sequentially added and the mixture was stored at 60° C. for 1 h. Dilution with water brought about the precipitation of ethyl 3,5-dimethyl-4-n-propylpyrrole-2-carboxylate 4d as a yellow solid, 22.4 g (29%), mp 98°–99° C. (lit. mp 99°–99.5° C.) after recrystallization from ethanol; $^1$H NMR (CDCl$_3$): δ 9.3 (s, 1H), 4.25 (q, 2H), 2.25 (t, 2H), 2.24 (s, 3H), 2.1s (s, 3H), 1.41 (m, 2H), 1.30 (t, 3H), 0.90 (t, 3H). The procedure was extended to the conversions of (a) 3-n-butyl-2,4-pentanedione to ethyl 3,5-dimethyl-4-n-butylpyrrole-2-carboxylate 4e, a yellow solid, 32%, mp 99°–100° C. (lit. mp 99° C.), $^1$H NMR (CDCl$_3$): δ 9.35 (S, 1H), 4.27 (q, 2H), 2.50 (t, 2H), 2.25 (s, 3H), 2.15 (s, 3H), 1.40 (m, 4H), 1.31 (t, 3H), and 0.91 (t, 3H); (b) 3-isopropyl-2,4-pentanedione to ethyl 3,5-dimethyl -4-isopropylpyrrole-2-carboxylate 4f , 20%, mp 104°–106° C. (lit. mp 105°–106.5° C.); and (c) 2-acetylcyclohexanone to ethyl 3-methyl-4,5,6,7-tetrahydroinadole-2-carboxylate 4i, 50%, mp 111°–113° C. (lit. 110° C.), $^1$H NMR (CDCl$_3$): δ 9.03 (s, 1H), 4.25 (q, 2H), 2.41 (m, 4H), 2.21 (s, 3H), 1.65 (m, 4H), 1.30 (t, 3H).

Ethyl 3,5-dimethyl-4-tert-butylpyrrole-2-carboxylate 4g. A solution of acetic acid (5.0 ml), sulfuric acid (1.2 ml), ethyl 3,5-dimethylpyrrole-2-carboxylate 5a (5.0 g, 0.03 mol) and tert-butyl acetate (3.5 g, 0.03 mol) was heated at 75° C. for 2 h and combined with sodium carbonate (8 g) in ice water (100 ml) to bring about the precipitation of ethyl 3,5-dimethyl-4-tert-butylpyrrole-2-carboxylate 4g as a colorless solid, mp 108°–110° C. (lit. 107°–109° C.), 3.1 g (47%); $^1$H NMR (CDCl$_3$): δ 9.80 (s, 1H), 4.28 (q, 2H), 2.43 (s, 3H), 2.39 (s, 3H), 1.35 (s, 9H), 1.33 (t, 3H).

Ethyl 3-methyl-2,4,5,6-tetrahydrocyclopenta[c]pyrrolecarboxylate 4j. A procedure for the synthesis of pyrroles via N-(3-oxo-1-alkenyl)glycine ester was adapted from Hombrecher and Horter, Synthesis 389, 1990. Ethyl aminoacetate hydrochloride (28 g, 0.20 mol) and triethylamine (20.1 g, 0.20 mol) were added to a solution of 2-acetylcyclopentanone (25.0 g, 0.20 mol) in ethanol (400 ml). The solution was stirred at room temperature for 15 hours and concentrated. The residue was combined with water (250 ml), and extracted with methylene chloride (4×100 ml). The combined extract was washed with water (100 ml), dried (sodium sulfate), and concentrated to leave a light brown oil. The oil was added with stirring at 50° C. to a solution of sodium ethoxide (14 g, 0.20 mol) in absolute ethanol (400 ml). The mixture was heated at 80° C. for 3 hours and poured into water (500 ml) to precipitate a light yellow solid. Recrystallization from ethanol gave ethyl 3-methyl-2,4,5,6-tetrahydrocyclopenta[c]pyrrolecarboxylate 4j, 9.1 g (24%) as a pale yellow solid, mp 166°–167° C.; $^1$H NMR (CDCl$_3$): δ 8.38 (s, 1H), 4.24 (q, 2H), 2.78 (t, 2H), 2.52 (t, 2H), 2.30 (m, 2H), 2.18 (s, 3H), 1.30 (t, 3H). Anal. calcd for C$_{11}$H$_{15}$NO$_2$: C, 68.39; H, 7.77; N, 7.25. Found, C, 68.40; H, 7.85; N, 7.15.

2-Trifluoroacetyl-3,5-dimethylpyrrole 12. Trifluoroacetic anhydride (15.8 g, 75 mmol) was added dropwise with stirring to a solution of 2,4-dimethylpyrrole 5a (9.6 g, 50 mmol) in benzene (140 ml) at 0° C. The mixture was stored at 0° C. for 3 h and washed with water (25 ml). The separated organic layer was dried (magnesium sulfate), concentrated, and chromatographed (silica gel, hexane|ethyl acetate, 3/1) to give 2-trifluoroacetyl-3,5-dimethylpyrrole 12 as a colorless solid, mp 80° C., 10.6 g (55%); IR (KBr): υ) 3309, 1630,1563, 1500, 1443, 1227, 800; $^1$H NMR (CDCl$_3$): δ 5.9 (s, 1H), 2.35 (bs, 6H). Anal. calcd for C$_8$H$_8$NOF$_3$: C, 50.26; H, 4.18;. N, 7.32; F, 29.84. Found: C. 50.27; H, 4.28; N, 7.16; F, 29.92.

Phosphoric acid method for the conversion of ethyl pyrrole-2-carboxylates to α-unsubstituted pyrroles. 2,4-Dimethyl-3-isopropylpyrrole 5f. Ethyl 3,5-dimethyl-4-isopropylpyrrole-2 carboxylate 4f (8.4 g, 40 mmol) as a melt at 100° C. was treated with phosphoric acid (85%, 20 ml) The mixture was heated at 160° C. for 30 min and combined with aqueous sodium hydroxide (200 ml, 200 mmol). Distillation gave 1175 ml that was extracted with diethyl ether (3×100 ml). The organic phase was dried (magnesium sulfate) and concentrated to give a dark brown oil. Distillation gave 2,4-dimethyl-3-isopropylpyrrole 5f as a colorless oil, 1.6 g (30%), bp 65°–66° C. (10 mm). IR (KBr): υ 2296, 1684, 1591, 1448, 1094; $^1$H NMR (CDCl$_3$): δ 6.4 (s, 1H), 2.3 (s,3H), 2.2 (s, 3H), 1.9 (m, 1H), 1.0 (d, 6H). Anal. calc. for C$_9$H$_{15}$N: C, 78.83; H, 10.94; N, 10.21. Found: C, 78.69; H, 10.87; N, 10.12.

In similar reactions with phosphoric acid: (a) ethyl 3,5-dimethyl-4-n-propylpyrrole-2-carboxylate 4d converted to 2,4-dimethyl-3-n-propylpyrrole 5d, 54%, as a semi-solid, (lit. [32] mp 13.5° C.), $^1$H NMR (CDCl$_3$): δ 7.30 (s, 1H), 6.25 (s, 1H), 2.40 (t, 2H), 2.15 (s, 3H), 2.00 (s, 3H), 1.30 (m, 2H), 0.90 (t, 3H); (b) ethyl 3,5-dimethyl-4-n-butylpyrrole-2-carboxylate 4e to 2,4-dimethyl-3-n-butylpyrrole 5e as an oil 48%, $^1$H NMR (CDCl$_3$): δ 7.45 (s, 1H), 6.30 (s, 1H), 2.30 (t, 2H), 2.15 (s, 3H), 2.01 (s, 3H), 1.40 (m, 4H), 0.90 (t, 3H); and (c) ethyl 3-methyl-4,5,6,7-tetrahydroindole-2-carboxylate 4i to 3-methyl-4,5,6,7-tetrahydroindole 5i, 53%, mp 55°–57° C. (lit. 58° C.), $^1$H NMR (CDCl$_3$): δ 7.30 (s, 1H), 6.31 (s, 1H), 2.47 (m, 4H), 2.05 (s, 3H), 1.82 (m, 4H).

2,4-Dimethyl-3-tert-butylpyrrole 5g. A procedure reported for the decarboxylation of derivatives of pyrrole-3-carboxylic acid was adapted from Clue, J. Org. Chem. 19:266, 1954. A solution of ethyl 3,5-dimethyl-4-tert-butylpyrrole-2-carboxylate 4g (3.0 g, 0.01 mol) and potassium hydroxide (6.0 g, 0.11 mol) in ethanol (50 ml) was heated at 80° C. for 4 h, combined with ice water (200 ml), and made slightly acidic by the addition of acetic acid to bring about the precipitation of crude 3,5-dimethyl-4-tert-butylpyrrole-2-carboxylic acid 4 (W=CH$_3$, X=C(CH$_3$)$_3$, R=CO$_2$H). The crude acid was combined with ethanolamine (5 g), heated at 180° C. for 1 h, and diluted with ice water (100 ml) to bring about the precipitation of 2,4-dimethyl-3-tert-butylpyrrole 5g as a colorless solid, 1.6 g (79%), mp 70°–71° C. (lit. 69°–71° C.) after drying in a vacuum for 24 h; $^1$H NMR (CDCl$_3$): δ 7.60 (br, 1H), 6.30 (s, 1H), 2.25 (s, 3H), 2.15 (s, 3H), 1.28 (s, 9H). By the phosphoric acid method the pyrrole ester 4g was converted to 2,4-dimethylpyrrole 5a.

3-Methyl-2,4,5,6-tetrahydrocyclopenta[c]pyrrole 5j. A solution of ethyl 3-methyl-2,4,5,6-tetrahydrocyclopenta[c]pyrrolecarboxylate 4j (9.1 g, 0.04 mol) and potassium hydroxide (26 g, 0.47 mol) in ethanol (200 ml) was heated at 80° C. for 4 hours and concentrated. The residue was combined with ice water (400 ml), and made slightly acidic by the addition of acetic acid to bring about the precipitation of crude 3-methyl-2,4,5,6-tetrahydrocyclopenta[c]pyrrolecarboxylic acid. The crude acid was combined with ethanolamine (5 g), heated at 180° C. for 1 hour, and diluted with ice water (100 ml). Extraction by methylene chloride (3×100 ml) followed by solvent removal and distillation of a residual oil, bp 110°–111° C. (20 mm) gave 3-methyl-2,4,5,6-tetrahydrocyclopenta[c]pyrrole 5j, 3.6 g (64%) as a colorless oil; $^1$H NMR (CDCl$_3$): δ 7.57 (s, 1H), 6.33 (s, 1H), 2.67 (t, 2H), 2.59 (t7 2H), 2.35 (m, 2H), 2.22 (s, 3H). Anal. calcd for C$_8$H$_{11}$N: C, 79.34; H, 9.09; N, 11.59. Found: C, 79.12; H, 9.29; N, 11.60.

2,6-Di-n-propyl-1,3,5,7,8-pentamethylpyrromethene-BF$_2$ complex 7d. Acetyl chloride (8.0 ml, 0.11 mol) was added dropwise over a period of 5 min. to a solution of 2,4-dimethyl-3-n-propylpyrrole 5d (7.0 g, 0.05 mol) in dichloromethane (5 ml). The reaction mixture was heated at 40° C. for 1 h, cooled to 25° C. diluted with hexane (250 ml), triturated, and decanted. The residue, presumed to be crude 3,5,3',5',6-pentamethyl-2,6-di-n-propylpyrromethene hydrochloride 6d, was treated without further purification with ethyldiisopropyl amine (45 g) (triethyl amine was also effective) in toluene (300 ml) and stirred 15 min. After boron trifluoride etherate (40.8 ml, 0.33 mol) was added dropwise with stirring the solution was heated at 40° C. for 1 h, washed with water (200 ml), dried over magnesium sulfate, and concentrated to give a dark brown solid. Flash chromatographic purification (twice, silica gel, 300 g, 230–400 mesh, 60 Å, toluene) followed by concentration of the green-yellow fluorescent fraction gave the P-BF$_2$ 7d as a solid, 1.8 g. Further characterization and examples of similar conversions of pyrroles 5e–5n to P-BF$_2$ derivatives 7e–7n are described in Tables VI and VII.

When acetyl chloride was replaced with propionyl chloride, isobutyryl chloride, cyclohexanecarbonyl chloride, acetoxyacetyl chloride, and p-dimethylaminobenzoyl chloride similar reaction sequences converted kryptopyrrole 5c to 8-ethyl, 8-isopropyl, 8-cyclohexyl, 8-acetoxymethyl, and 8-dimethylaminophenyl derivatives 7o–s of 1,3,5,7-tetramethyl-2,6-diethylpyrromethene-BF$_2$ complex 7 (X=Z=CH$_3$, Y=CH$_2$CH$_3$). Treatment with p-anisoyl chloride followed by boron trifluoride etherate converted 2,4-dimethylpyrrole 5a to 1,3,5,7-tetramethyl-8-p-methoxyphenylpyrromethene-BF₂ complex 7t. The properties of the products 7o-t are described in Tables VI and VII.

Pyrromethene Hydrobromides and BF₂ Complexes. Crude pyrromethene hydrobromides 6 were obtained from α-pyrrole carboxylate esters 4 (Kleinspehn, 1955) and converted without purification to P-BF₂ dyes 7. A mixture of ethyl 3-phenyl-4-ethyl-5-methylpyrrole-2-carboxylate 4o (2.57 g, 10 mmol), hydrobromic acid (3 ml, 48%) and formic acid (3.5 g) was heated at 100° C. for 4 h. The reaction mixture was cooled to 0° C. to bring about the separation of crude 3,3'-diphenyl-4,4'-diethyl-5,5'-dimethylpyrromethene hydrobromide 6u 1.3 g (55%) mp 235° C. (dec); ethyl 3,4-diphenyl-5-methyl-pyrrole-2-carboxylate 4p gave crude 3,4,3',4'-tetraphenyl-5,5-dimethylpyrromethene hydrobromide 6v (75%) mp 280° C. (dec) (lit. mp 280° C. (dec)); and ethyl 3-phenyl-4-acetyl-5-methylpyrrole-2-carboxylate 4q gave crude 3,3'-diphenyl-4,4'-diacetyl-5,5'-dimethylpyrromethene hydrobromide 14 (50%) mp 230° C. (dec). In similar conversions 3,5-dimethyl-4-tert-butyl-pyrrole-2-carboxylate 4g gave crude 3,5,3',5'-tetramethyl-2,6-di-tert-butylpyrromethene hydrobromide 6x and ethyl 3,4-diethyl-5-methylpyrrole-2-carboxylate 4k gave crude 3,4,3',4'-tetraethyl-5,5'-dimethylpyrromethene hydrobromide 6y.

Each salt 6u, v, x, y and 14 was converted by treatment with boron trifluoride etherate as described above to the corresponding P-BF₂ dye 7u, v, x, y, and 7w (see Table II). Treatment of the pyrromethene hydrobromide 14 by boron trifluoride etherate also brought about deacylation. This may have occurred initially to give 3,3' diphenyl-5,5'-dimethylpyrromethene hydrobromide 6w as the precursor to the P-BF₂ derivatives 7w or after an initial formation of undetected 1,7-diphenyl-2,6-diacetyl-3,5-dimethylpyrromethene-BF₂ complex 7 (X=C₆H₅, Y=COCH₃, W=H, Z=CH₃).

1,3,5,7-Tetramethyl-2,6-diethyl-8-cyanopyrromethene-BF₂ complex 7bb. Ethyl 3,5-dimethyl-4-ethyl-pyrrole-2-carboxylate 4c was converted to 3,5,3',5'-tetramethyl-4,4'-diethylpyrromethene hydrobromide 9, mp 230°–246° C. (dec) by the process described above. A mixture of the pyrromethene hydrobromide 9 (7.75 g, 0.02 mol) and potassium cyanide (5.6 g, 0.084 mol) in ethanol (85%, 70 ml) was heated at 80° C. with stirring for 45 min, cooled to 40° C., and diluted with water (80 ml) to bring about the precipitation of a pale brown solid. Flash chromatography on silica gel (300 g, 230–400 mesh, 60 Å dichloromethane) gave an impure sample of 3,5,3',5'-tetramethyl-4,4'-diethyl-6-cyanopyrromethane 15, 2.5 g, 44%, mp 110°–114° C. IR (KBr): υ 2238 (CN). The impure pyrromethane 15 in chloroform was chloroform at 25° C. over a period of 5 min. Removal of solvent left 3,5,-3,5'-tetramethyl-4,4'-diethyl-6-cyanopyrromethene hydrobromide 6bb. Without purification it was treated with boron trifluoride etherate (general procedure above) for conversion to 1,3,5,7-tetramethyl-2,6-diethyl-8-cyanopyrromethene-BF₂ complex 7bb.

EXAMPLE V

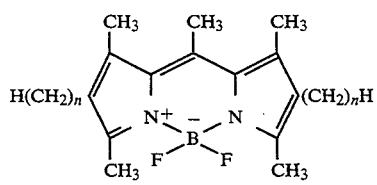

An alternation effect in the relative efficiency (RE) of laser activity in 1,3,5,7,8-pentamethyl-2,6-di-n-alkylpyrromethene-BF₂ dyes 20 depended on the number of methylene units in the n-alkyl substituent, —(CH₂)ₙH, to give RE ≧ 100 when n was even (=0, 2, 4) and RE 65, 85 when n was odd (=1, 3) (RE 100 arbitrarily assigned to the dye rhodamine-6G).

EXAMPLE VI

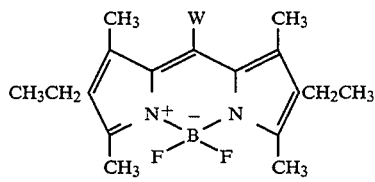

7p W= (CH₃)₂CH
7q W = (C—C₆H₁₁)

The absence of fluorescence and laser activity in 1,3,5,7-tetramethyl-2,6-diethyl-8-isopropylpyrromethene-BF₂ complex 7p and a markedly diminished fluorescence quantum yield (Θ0.23) and lack of laser activity in 1,3,5,7-tetramethyl-2,6-diethyl-8-cyclohexylpyrromethene-BF₂ complex 7q were attributed to molecular nonplanarity brought about by the steric interference between each of the two bulky 8-substituents with the 1,7-dimethyl substituents.

EXAMPLE VII

An atypically low RE 20 for a peralkylated dye without steric interference was observed for 1,2,6,7-bis-trimethylene-3,5,8-trimethylpyrromethene-BF₂ complex 7j.

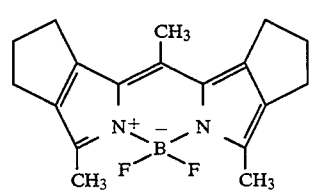

Comparisons with peralkylated dyes revealed a major reduction to RE 0–40 for six dyes lacking substitution at the 8-position.

EXAMPLE VIII

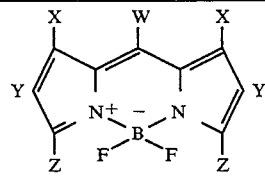

| | |
|---|---|
| 7l | W = X = Z = CH₃, Y = C₆H₅ |
| 7m | W = X = Z = CH₃, Y = NHCOCH₃ |
| 7n | W = X = Z = CH₃, X = OCH₃ |
| 7aa | W = CN, X = Z = CH₃, Y = CO₂C₂H₅ |
| 7bb | W = CN, X = Z = CH₃, Y = CH₂CH₃ |

Laser activity RE was diminished somewhat by functional group (polar) substitution in the 2,6-diphenyl derivative 7l, RE 20, and the 2,6-diacetamido derivative m, RE 5, and in 1,7-dimethoxy-2,3,5,6,8-pentamethyl-pyrromethene-BF₂ complex 7n, RE 30. Diethyl 1,3,5,7-tetramethyl-8-cyanopyrromethene-2,6-dicarboxylate- BF$_2$ complex 7aa and 1,3,5,7-tetramethyl-2,6-diethyl-8-cyanopyrromethene-BF$_2$ complex 7bb offered examples of P-BF$_2$ dyes with electron withdrawing substituents at the 8-position. The dye 7aa, $\lambda_{las}$ 617 nm, showed nearly twice the power efficiency that was obtained from rhodamine-B, $\lambda_{las}$ 611 nm.

EXAMPLE IX

New heterocycle-BF$_2$ dyes are needed to extend the spectral range of the P-BF$_2$ dyes disclosed above. These above disclosed dyes have a spectral range of 520–620 nm, but it would be advantageous to broaden this range to 300–800 nm. Communication devices utilizing laser beams camouflaged by sea water, for example, require photostable, water-soluble, highly efficient blue-green dyes with laser activity near 460 nm. Photodynamic therapy for cancer is preferably performed with dyes which have luminescence near 620 nm for maximum tissue penetration. In these and other examples success depends on laser beam tunability, a feature characteristic of organic laser dyes but not generally encountered in solid state lasers. Structures for such dyes are given below, along with synthesis procedures and methods of proposed spectroscopic evaluation.

EXAMPLE X

Imidazomethene-BF$_2$ Complexes (I-BF$_2$)

The tetramethyl-2,2'-biimidazole-BF$_2$ (complex 21)

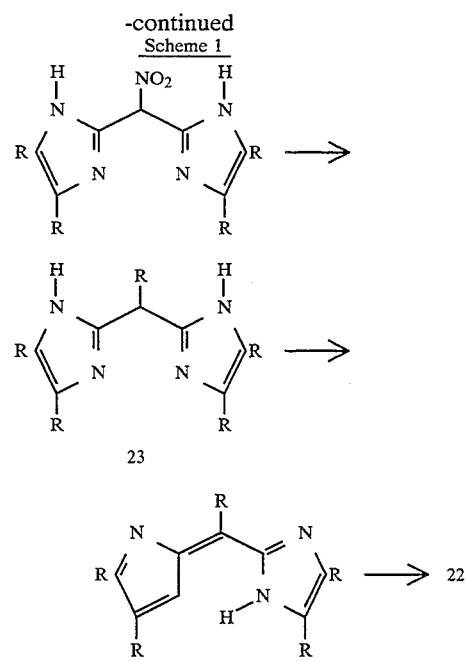

In part the method was adapted from a known preparation of the unsubstituted imidazomethane (R=H). Joseph et al., *Synthesis* 459, 1977. The final two steps (1)

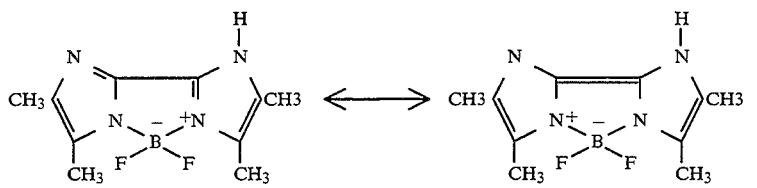

is related to but structurally different from the cyanines. The inventors have studied its Lewis acid salt 21-BF$_3$, $\lambda_f$ 377 nm $\Theta_f$ 0.93 for laser activity. It has an observed fluorescence at 377 nm, which predicts a red shift to $\lambda_f$~440 nm $\Theta_f$~0.9 for the more highly conjugated fluorophore in alkylated derivatives 28 of imidazomethene-BF$_2$ complexes (I-BF$_2$).

A preparation for I-BF$_2$ dyes 22

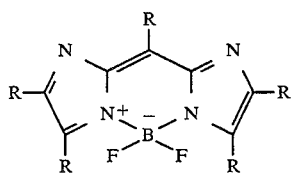

is outlined in Scheme 1.

oxidation by bromine and (2) chelation by treatment with boron trifluoride to give the complex 22 were adapted from a similar conversion of a pyrromethane to a pyrromethene-BF$_2$ complex.

EXAMPLE XI

8-Azapyrromethene-BF$_2$ (AP-BF$_2$) and 8-Azaimidazomethene-BF$_2$(AI-BF$_2$) Complexes Preparation of 3,3,5,7-tetraalkyl-8-azapyrromethene-BF$_2$ complex 26 is outlined in Scheme 2. A condensation reaction between hydroxylamine and a λ-oxopropionitrile 24 to give an azapyrromethene 25 was reported in Stetter, *Org. Syn.* 59:53 (1980). The latter boron trifluoride is treated to bring about the formation of the AP-BF$_2$ complex 26, as in the preparation of the P-BF$_2$ complex in Shah et al., *Heteroatom Chem.*, 1:389, 1990.

Scheme 1

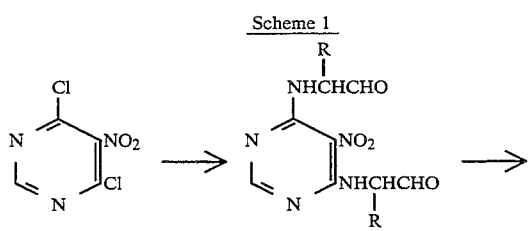

Scheme 2

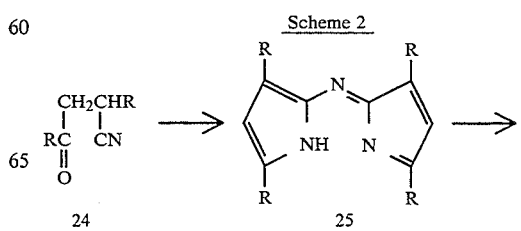

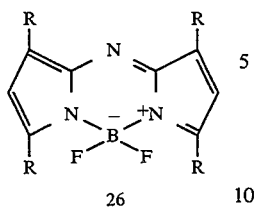

EXAMPLE XII

A somewhat different approach is proposed for the preparation of an alkylated 8-azaimidazomethene-$BF_2$ complex 27. The steps are outlined in Scheme 3. An alkylation of a 2-aminoimidazole by a 2-bromoimidazole gives a biimidazo-2-yl amine. Oxidation by bromine and chelation by treatment with boron trifluoride gives the AP-$BF_2$ complex 27.

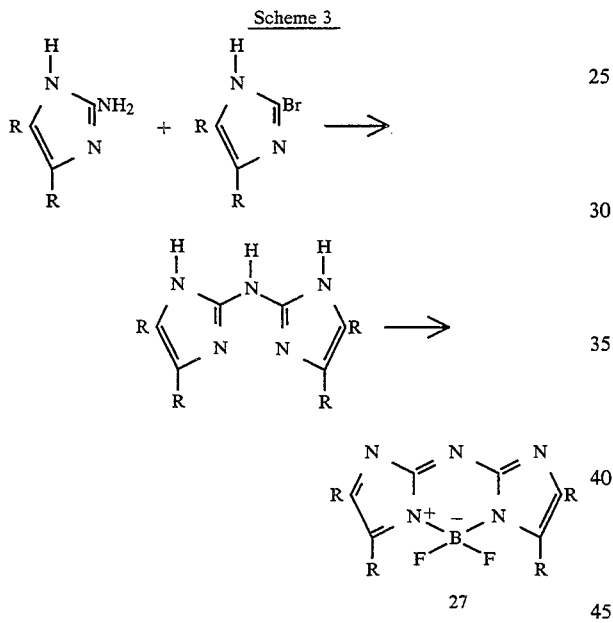

Scheme 3

Dipyridylamine-$BF_2$ (DPA-$BF_2$) and Dipyridylmethane-$BF_2$ (DPM-$BF_2$) Complexes A synthesis and characterization of α,α'-dipyridylamine-$BF_2$ complex 29 (R=H) was not found in the literature. Its straightforward proposed preparation by the reaction of α,α'-dipyridylamine 28 (R=H) with boron trifluoride is outlined in Scheme 4. The method may be extended to the alkylated derivatives (28 R=alkyl) of dipyridylamine.

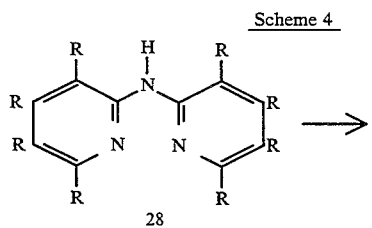

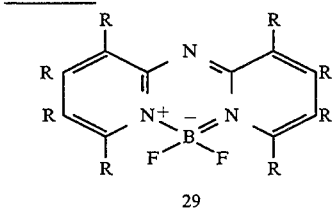

Scheme 4

The "boratriazinium" salt (≡29, R=H) showed $\lambda_{las}$ 420, hence the alkylated DPA-$BF_2$ derivatives 29 (R=methyl, ethyl, propyl, butyl, preferably n-alkyl) can be expected to lase at ~460 nm. This blue-green laser beam can be used for underwater communication by flashlamp dye excitation. The DPA-$BF_2$ dye (R=H) was reported to lase following excitation by a nitrogen laser, hence dye 29 may similarly be excited by a nitrogen laser, as in Basting et al., *Appl. Phys.*, 3:81, 1974.

A similar conversion is shown in Scheme 5, of an α,α'-dipyridylmethane 30 by treatment with boron trifluoride to form a DPM-$BF_2$ complex 31. These dyes are expected to fluoresce around 400–500 nm. They would be examined for response to flashlamp pulses and other means of excitation to produce laser activity.

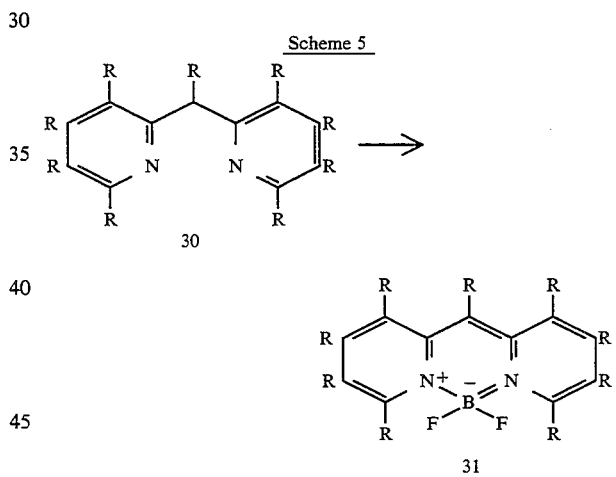

Scheme 5

EXAMPLE XIV

P-$BF_2$ with Fluorescence and Laser Activity above 600 nm

A red shift in the electronic spectra (absorption, fluorescence, and laser activity) of a dye molecule can be achieved by elongation of the system of conjugated double bonds in the chromophore. This elongation can be achieved by substitution in selected P-$BF_2$ dyes.

The preparation of 1,3,5,7-tetramethyl-8-cyano-2,6-dicyanovinylpyrromethene-$BF_2$ (complex 35) would require converting 3,5,3',5'-tetramethyl-4,4'-diiodo-6-cyanopyrromethane 33 to the corresponding 4,4'-dicyanovinyl derivative 34 by treatment with acrylonitrile in the presence of palladium acetate and triphenyl phosphine in a reaction patterned after the vinylation of aryl iodides. Dieck and Heck, *J. Amer. Chem. Soc.*, 96:1133, 1974.

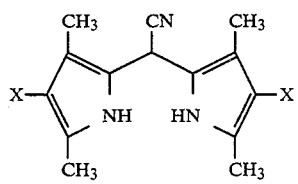

32 X = H
33 X = I
34 X = CH=CHCN

A general procedure for halogenation of pyrroles (Chadwick, Chapter 3.05, in Katritzky and Rees, *Comprehensive Heterocyclic Chemistry*, 4:213, 1984) is adapted for the conversion of the pyrromethane 32 to the dibromide or the diiodide 33. Concurrent oxidation to the corresponding pyrromethene is expected to occur. The conversion of compound 34 to the P-BF$_2$ derivative 35 will require a mild oxidative dehydrogenation of the pyrromethane to the corresponding pyrromethene followed by treatment with boron trifluoride (see Shaw et al., *Heteroatom Chem.*, 1:389, 1990).

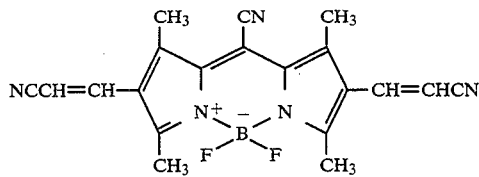

35

Chromophore elongation is also achieved by conversions of 1,5,7,8-tetramethyl-formyl-2,6-diethylpyrromethene-BF$_2$ complex 36 by the Wittig reaction. March, "Advanced Organic Chemistry," 4th ed., p. 956, 1992. This versatile method is general for the conversion of aldehydes into functionalized olefins. The aldehyde 36 is treated with a Wittig ylide derived from β-bromopropionitrile to produce 1,5,7,8-tetramethyl-3-cyanovinyl-2,6-diethylpyrromethene-BF$_2$ complex 37.

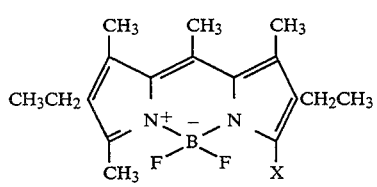

36 X = CHO
37 X = CH=CHCN

Fluorescence and laser activity of P-BF$_2$ dyes 35 and 37 and similar derivatives with other conjugated unsaturated substituents at the 2,6-positions are expected near 650 nm and above.

Other specific compounds of interest comprehended in the scope of this invention include:

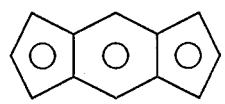

(s-indacene)

-continued

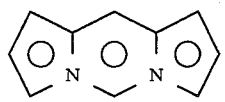

(ea, 4a-Diaza-s-indacene)

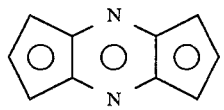

(4, 8-Diaza-s-indacene)

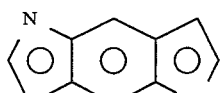

(3, 7-Diaza-s-indacene)

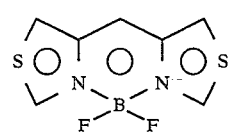

(2, 6-Dithia pyrromethene-BF2 complex)

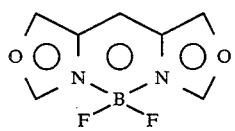

(2, 6-Dioxapyrromethene-BF2 complex)

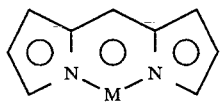

(Pyrromethene-metal complex)

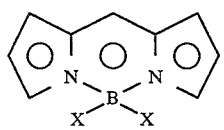

X = F, CnH2n + 1, phenyl, naphthyl or H (4, 4-Disubstituted-pyrromethene-B-complex)

USE OF THE COMPOSITIONS AS LASER DYES

As previously indicated, the compositions described herein function efficiently as laser dyes when used with conventional dye laser systems. For example, an exemplary laser with which the compositions of the invention may be used includes a flashlamp-pumped dye laser system manufactured by the E.G. & G. Corporation (Model No. FX139C-2). This system has a flashlamp capable of producing pulses of approximately 200 ns risetime and 600 ns length at the half-width of the pulse. It is also capable of delivering 2 Joules at 6.32 kV, 5 Joules at 10.0 kV, and 10 Joules at 14.14 kV. The cell or containment vessel used in the system to retain the dye is about 2.5 mm in diameter and about 50 mm long.

As far as solvents for the compounds are concerned, the data in Tables I and II is of importance. With respect to the compounds of Examples I and II, CH$_3$OH and $H_2O$ respectively are preferred as solvents. Preferred solvents for solubilizing any of the compounds in this application may be determined by performing the solubility and fluorescence tests on them as in Tables I and II. In alternative systems, the compounds of the invention used as laser dyes may be in a gaseous form, or homogeneously dispersed in a polymer slug (e.g. a plastic such as methyl methacrylate).

Upon excitation, the compounds produce laser light having a high quantum fluorescence yield with low triplet-triplet (T—T) absorption, as well as a high degree of photostability. This improves the overall efficiency of the laser systems with which the dyes are used in comparison with previously used dye materials.

Preferred compounds for use as laser dyes which are encompassed in the scope of this invention include those compounds with a structure:

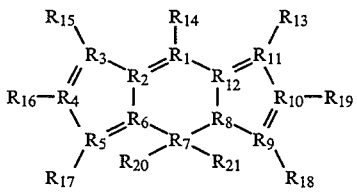

wherein the substitutions are those listed in the Summary of the Invention.

In a preferred embodiment, $R_1$-$R_5$ and $R_9$-$R_{12}$=C.

In other embodiments, $R_1$-$R_5$ and $R_9$-$R_{12}$=C and $R_{13}$=$R_{15}$=$R_{17}$=$R_{18}$=$C_nH_{2n+1}$ where n=1-3.

In yet other preferred embodiments, $R_1$-$R_5$= $R_9$-$R_{12}$=C; $R_{13}$=$R_{15}$=$R_{17}$=$R_{18}$=$C_nH_{2n+1}$ where n=1-3; and $R_6$=$R_8$=N.

In more preferred embodiments, $R_1$-$R_5$= $R_9$-$R_{12}$=C; $R_{13}$=$R_{15}$=$R_{17}$=$R_{18}$=$C_nH_{2n+1}$ where n=1-3, $R_6$ and $R_8$=N and $R_7$=B.

In yet other preferred embodiments, $R_1$-$R_5$= $R_9$-$R_{12}$=C; $R_{13}$=$R_{15}$=$R_{17}$=$R_{18}$=$C_nH_{2n+1}$ where n=1-3; $R_6$=$R_8$=N; $R_7$=B; and $R_{20}$=$R_{21}$=F.

In most preferred embodiments, $R_1$-$R_5$=$R_9$-$R_{12}$=C; $R_{13}$=$R_{15}$=$R_{17}$=$R_{18}$=$C_nH_{2n+1}$ where n=1-3, $R_6$=$R_8$=N; $R_7$= B and $R_{20}$, $R_{21}$=F and $R_{16}$ and $R_{19}$=H, $NaSO_3$ or $C_nH_{2n+1}$ where n=1-4.

EXAMPLE XV

Under synchronous pumping by a mode-locked Coherent Antares Nd: YAG laser, the dye 1,3,5,7,8-pentamethyl-2,6-diethylpyrro-methene-$BF_2$ complex (PMDEP-$BF_2$) gave twice the power output efficiency obtained from rhodamine 6G. PMDEP-$BF_2$ showed a photostability lifetime of 500 W-hours.

Similar results from tests in a Candela LFRDL 20 linear flashlamp dye laser showed the dye PMDEP-$BF_2$ to have 173% of the power efficiency of R-6G.

In a continuous wave (CW) operation with an argon ion pump laser (5 watts all lines 457.9-514.5 nm) the disodium salt of 1,3,5,7,8-pentamethylpyrromethene-2,6-disulfonic acid-$BF_2$ complex PMPDS-$BF_2$ gave 45% power output as 32%. Under flashlamp excitation pulses the photostability in methanol of PMPDS-$BF_2$ (9000 pulses) was six times greater than that for R-6G (1500 pulses).

In a technological breakthrough P-$BF_2$ dyes homogeneously dispersed in an acrylic copolymer were found to be superior "solid-state" lasers with the special feature of tunability characteristics of a laser dye. PMDEP-$BF_2$ ($10^{-4}$M) in a polymer matrix (5 parts methyl methacrylate and 1 part hydroxypropyl acrylate) gave a power efficiency of 88%. R-6G under similar treatment gave an unsatisfactory performance and was not measured; sulforhodamine-B gave a 37% efficiency. Similar tests showed other P-$BF_2$ dyes to rival PMDEP-$BF_2$ in efficiency.

In a typical measurement of the P-$BF_2$ chromophore T—T absorption for the dye PMPDS-$BF_2$ was barely detectable ($\epsilon_T \sim 3 \times 10^{-3}$) in the fluorescent spectral area.

PHOTODYNAMIC THERAPY

Light Source

Almost any light source can be used for photodynamic therapy. Lasers (specifically argon-pump dye lasers) can be used to produce light that is used to illuminate the targeted tissue area of the present invention. The laser is coupled to one or more fiberoptic cables to propagate light to the tip, with minimal energy loss. The tip may be cleaved for forward light projection; it may be bulb tipped for isotropic spherical distribution; or a cylindrical scattering material can be applied to the fiber tip to distribute light perpendicularly to the fiber axis. The energy delivered will depend on the dosage (the amount of light and the duration of its delivery) of light from the fiber. Before treatment, the light distribution can be calibrated at the tip with a power meter; the dosage of light delivered is preferably gauged to prevent any hyperthermic effects.

A most preferred wavelength of the light can be determined from the fluorescence (FL) spectra of the cytotoxic compounds, as in FIG. 2 for PMP-$BF_2$. Incident light having a wavelength of about 500-550 nm produced the greatest fluorescence. That would be the most preferred wavelength for light used to illuminate PMP-$BF_2$ in photodynamic therapy. Similar preferred wavelengths can be readily determined for the other compounds of the present invention.

Targets for Photodynamic Therapy

Photodynamic therapy (PDT) causes early, significant damage to membranes, particularly the plasma membrane, with the formation of multiple membrane blebs. These blebs protrude from the cell membrane and indicate severe membrane damage. This membrane damage is an early observable effect of the cytotoxicity induced by the method of the present invention. The term "cytotoxicity" is used in its well-known and commonly accepted medical sense to mean damage to cells. The histologic effects of tumors treated with the photodynamic therapy of the present invention characteristically exhibit an avascular necrosis.

Sensitizer Dose

There is no critical dosage of drug which must be delivered to provide the cytotoxic effect of the present invention. There is an expected increase in the amount of cytotoxicity as the dose of the drug increases. A preferred systemic dose of 1.5-2.5 mg/kg of subject weight has been found suitable to induce cytotoxic damage in living cells following exposure to a light source, such as a sunlamp, laser, or fiberoptic scope.

Target Tissues

The photodynamic therapy of the present invention can be used to induce cytotoxic damage to many different types of living tissue. The cytotoxic damage induced by the present method occurs without respect to the tissue type, histologic characteristics, or the presence of receptors. The method is especially useful in treating patients with tumors in numerous anatomic sites, including the skin, bronchus, bladder, esophagus, brain, and gynecological and intra-abdominal tissues.

Specific examples of skin malignancies in which the cytotoxic effect of the present invention would be useful include basal and squamous cell cancers, malignant melanoma, Kaposi's sarcoma, mycosis fungoides, metatastic epidermoid, and recurrent breast cancer. Head and neck cancers that can be treated with the present method include nasopharyngeal, tongue and other oropharyngeal tumors.

Other target tissues include transitional cell carcinoma of the bladder, endobronchial cancer (such as adenocarcinoma or small cell carcinoma), esophageal cancer (such as adenocarcinoma), gynecologic tumors (such as cervical carcinoma in situ, vaginal cancer and vulvar malignancies) and even brain tumors such as glioblastoma, astrocytoma and metatastic malignancies (such as lung cancer metatastic to the brain).

Use of the Compounds in Photodynamic Therapy

Testing has shown that administration of the materials to a subject, followed by excitation of a targeted tissue area using an appropriate light source can result in cytotoxic damage to or destruction of targeted tissue. Systemic intravenous introduction of the compound is preferably administered in a dosage of 1.5–2.5 mg/kg of the subject's body weight, more preferably 2.0 mg/kg.

Introduction of the compositions into the body of a subject is accomplished preferably by injection directly into the tumor or by topical application to the affected area. The compound is preferably provided in a 25 mg/ml sterile water solution that can be injected into the tumor or administered intravenously for systemic dosages. For topical application, a one ml amount of a 25 mg/ml or 0.3% solution can be thinly coated on an external area of the body to be treated, and then exposed to a light source either immediately or after a few hours.

Upon IV administration, the drug spreads throughout the body and into regions of diseased tissue (e.g., cancer tissue). Thereafter, the diseased target tissue is illuminated using light from a conventional light source (e.g., laser, sun lamp, etc.). In cases of cancer wherein the neoplastic growths are relatively near the skin surface, the light is applied directly through the skin. In other cases where neoplasms are deeper within the body (e.g., in the urinary bladder, gastrointestinal tract, respiratory tract, etc.) the light would be introduced by non-surgical or surgical entry into the body. For example, if the diseased tissue is in the respiratory tract, access could be accomplished by either surgical or non-surgical entry through the mouth using a fiber optic illumination system or the like.

Activation of the compounds by illumination with an appropriate light source results in photochemical processes which destroy diseased tissues. A collimated beam of light (such as a laser) is particularly preferred because a limited area of the body (such as the tumor) can be exposed to the light without illuminating surrounding tissue.

A specific example of this procedure is described with reference to breast cancer as follows:

EXAMPLE XVI

Breast tumors were induced in fifty-day-old female Sprague Dawley rats by the oral feeding of dimethylbenzanthracene (DMBA) in peanut oil. Individual rats were fed 10 mg DMBA per 100 g body weight via gavage tubes. Palpable tumors developed 45 to 92 days after feeding. The disodium salt of 4,4-difluoro-1,3,5,7,8-pentamethyl-4-bora-3a,4a-diaza-s-indacene-2,6-disulfonic acid monohydrate (PMPDS-BF$_2$) was synthesized as described in Example II above. Following tumor development, tumors were measured and injected with PMPDS-BF$_2$ dissolved in saline (x $\mu$g/ml). PMPDS-BF$_2$ was injected into the center of the tumors to a concentration of 20 $\mu$g/cm$^3$ of tumor volume.

Twenty-four hours after intratumor injection, the rats were anesthetized using phenobarbital (2 mg/kg i.p.) and the injected tumors were exposed to light from either a quartz lamp (100 or 250 w) or an argon laser (with 488/514 and 628 nm frequencies) for 10–20 minutes. Also included in this experiment were three control groups: (1) saline injected, unirradiated tumors; (2) saline injected, irradiated tumors; (3) PMPDS-BF$_2$ injected, and unirradiated tumors. Tumor necrosis was observed in those tumors injected with PMPDS-BF$_2$ and 50–100% tumor remission was seen in these cases. Tumors injected with PMPDS-BF$_2$ that were not irradiated and tumors which were injected with saline solution and received irradiation showed no necrosis or remission. The data from this experiment is presented in Table VIII below.

TABLE VIII

ANTI-TUMOR ACTIVITY OF DISODIUM SALT OF
PENTAMETHYLPYRROMETHENE-2,6-DISULFONATE BORON DIFLUORIDE
(PMPDS-BF$_2$)
(FOUR WEEKS AFTER INTRATUMOR INJECTIONS)*
All tumors evaluated had an initial total volume of 1 cm$^3$ or less.

| TREATMENT* | NO. ANIMALS EVALUATED | INITIAL MEAN TUMOR VOLUME (cm$^3$) | TOTAL TUMOR NO. | FINAL TUMOR MEAN TUMOR VOLUME (cm$^3$) | FINAL TUMOR NO. | COMPLETE RESPONSE (ANIMALS) |
|---|---|---|---|---|---|---|
| CONTROL (Saline) | 19 | 0.2 | 21 | 1.9 | 35 | 0/19 |
| PMPDS-BF$_2$ 20 ug/cm$^3$ plus light** | 10 | 0.3 | 14 | 0.1 | 3 | 7/10 |
| PMPDS-BF$_2$ 20 ug/cm$^3$ | 10 | 0.2 | 12 | 0.7 | 13 | 2/10 |
| Light Only** | 10 | 0.4 | 11 | 1.7 | 31 | 0/10 |

*Treated once.
**Quartz lamp — 100 watt exposure for 20 min.

Although not wishing to be bound by theory, applicants believe that the compounds described herein, including the product of Example II, reacts in a singlet state with tissue according to the first reaction mechanism (Type I) described above. Any of the compounds of the present invention could similarly be injected into the tumor at a dose of 2 μg/cm³ of the tumor and irradiated with the light sources of this example to induce cytotoxic injury in cells.

EXAMPLE XVII

Ovarian Cancer Cell Line 1,3,5,7,8-pentamethylpyrromethene-boron difluoride-2,6-disodium disulfonate salt (PMPDS-BF₂) and bimane diphosphonate were prepared according to previously described methods.

Human ovarian cells from fifteen individual patients were evaluated. All cancers were epithelial originating ovarian adenocarcinomas. Each cancer had been passed through at least one culture in RPMI-1640 (10% FBA) medium prior to use in the present study. In each case cells were harvested and washed in RPMI-1640 medium and resuspended in concentrations of $2.6 \times 10^6$ cells/ml at 5° C. The cells ($2.6 \times 10^6$ cells/ml) were then incubated in a RPMI-1640 growth medium (containing 10% fetal bovine albumin, penicillin 100 U/ml and streptomycin 100 μg/ml) pH, 7.4 with graded doses of PMPDS-BF₂ complex for 30 minutes at 37° C. in a 5% $CO_2$/air incubator with gentle shaking. The three concentrations of PMPDS-BF₂ evaluated in this study were 0.004 μg, 0.04 μg, and 0.4 μg/ml of medium. The cell suspension was then washed with cold RPMI-1640 medium to remove extracellular PMPDS-BF₂ complex, and then the cells were resuspended in fresh RPMI growth medium. Fifteen (15) ml portions of the cell suspensions ($2.6 \times 10^6$ cells/ml) were irradiated in glass tubes at 37° C. in room air over a 10–20 minute period using a General Electric sun lamp. Controls were cells exposed to PMPDS-BF₂ with no light exposure, cells with light exposure alone and cells with neither exposure to light nor chemicals.

Under identical conditions as above, bimane diphosphonate was evaluated for cytotoxic activities in the presence and absence of light. After the above incubations with PMPDS-BF₂ or bimanes±light as controls, melted Bacto-agar (Difco Laboratories, Inc., Detroit, Mich.) was added to the cell suspensions to a final concentration of 0.3% agar. The mixtures were plated in 35 mm plastic tissue culture dishes on a feeder layer containing an enriched McCoy's 5A medium and 0.5% agar with the addition of 2-mercaptoethanol (5 mM) and DEAE-dextran. The seeding density for the cells in this study was kept between $1-5 \times 10^4$ cells per dish and the plates incubated at 37° C. in a $CO_2$ incubator. Incubation was continued for another 2–3 weeks and the plates examined under an inverted phase contrast microscope and cells counted. Since these cells grow as tight aggregates in soft-agar, it was impossible to determine the number of cells in each growth. Instead, an ocular micrometer was used to count colonies 30 μm or larger in size. Plating efficiency, defined as the number of colonies formed per 100 viable cells plated, was compared between groups.

These results are shown in FIG. 3. Within forty-eight (48) hours after exposure to PMPDS-BF₂ (0.004 μg/ml) plus light, the ovarian cells demonstrated pyknotic changes with nuclear fragmentation. When compared to controls, 40–70% inhibition in cell growth was observed for all cancers tested at the 0.004 μg/ml concentration. PMPDS-BF₂ in concentrations of 0.4 μg/ml of media produced 100% inhibition of cell growth for all tumors tested. PMPDS-BF₂ controls in the absence of light exposure did not demonstrate significant cytotoxic responses.

The bimane diphosphonate in concentrations of 0.4 μg/ml, under identical conditions to the above using PMPDS-BF₂, produced only 10–30% cell inhibition in the ovarian cancer cells studied.

Ovarian cancer cells three days post exposure to PMPDS-BF₂ (0.04 μg/ml) plus light were unable to colonize, demonstrated pyknotic changes in the nucleus and cytoplasmic discoloration. The cells retained a yellow-green color for up to four (4) weeks and failed to colonize when resuspended in fresh medium and did not initiate cellular division. With time the cells disintegrated into cellular debris.

PMPDS-BF₂ or the bimane sulfonate without light did not produce cytotoxicities.

EXAMPLE XVIII

The following case history also illustrates topical application of one of the compounds of the present invention in a 71 year old black female with a 12-year history of metastatic breast cancer spread to the chest wall. The patient had been treated with combinations of numerous chemotherapeutic agents and radiation therapy. Her cancer continued to progress and she received nine weekly treatments with a topical 0.3% solution of 1,3,5,7,8-pentamethylpyrromethene boron difluoride-2,6-disulfonate (PMPDS-BF₂) in dimethylsulfoxide applied to the chest wall lesions followed by exposure to a General Electric sunlamp for ten minutes. The patient had initially a greater than 50% shrinkage of her tumor, which lasted over nine weeks. She demonstrated no toxic reactions. After a nine week shrinkage, the metastatic lesions again began to grow.

For PDT, any of the compounds of the present invention are used as in Example X–XII.

As used in this specification, the term "lower alkyl" refers to an alkyl group having 1–4 carbons. A class of substituents "selected independently" from a group means that any of the substituents can be any of the listed substituents and that the substituents in the class need not be identical (although they may be). The notation $R_1, R_2 \ldots R_x = A$, B or C or $R_1, R_2 \ldots R_x = A$, B or c shall be interpreted to mean that any R can be any of A, B or C.

The term "electron withdrawing group" means a group (such as a CN containing group) that withdraws electron density.

Having herein described a preferred embodiment of the invention, it is contemplated that suitable modifications may be made by those skilled in the art. For example, a variety of different compounds using the basic tri-cyclic structure presented herein may be used as laser dyes and/or photodynamic therapy agents. Thus, the invention shall only be construed in accordance with the following claims.

We claim:

1. A compound selected from the group consisting of:
   (a)

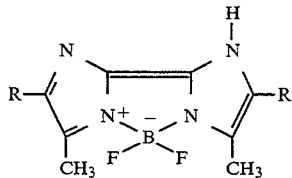

wherein R is H or lower alkyl;

(b)

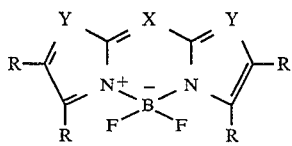

wherein X is CH or N, Y is CH or N, and R is lower alkyl, where at least one of X and Y is N; and (c) α,α′-dipyridylmethane-BF$_2$.

2. The compound of claim 1 wherein the compound is (a)

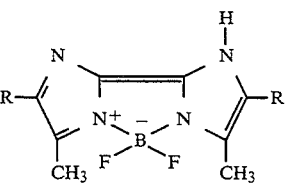

wherein R is H or lower alkyl; or (b)

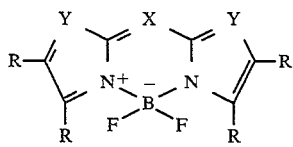

wherein X is CH, Y is N, and R is lower alkyl, where at least one of X and Y is N.

3. The compound of claim 2 wherein the compound is 2(a).

4. The compound of claim 2 wherein the compound is 2(b).

5. An imidazomethene-BF$_2$ complex according to the formula

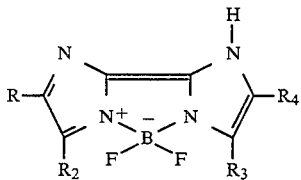

wherein R$_1$ and R$_4$ are H or lower alkyl and R$_2$ and R$_3$ are CH$_3$; or R$_1$–R$_4$ are lower alkyl.

6. The compound of claim 5 wherein the compound is tetramethyl-2,2′-biimidazole-BF$_2$.

* * * * *

UNITED STATES PATENT AND TRADEMARK OFFICE
CERTIFICATE OF CORRECTION

PATENT NO. : 5,446,157

DATED : August 29, 1995

INVENTOR(S) : Lee Roy Morgan, et al.

It is certified that error appears in the above-indentified patent and that said Letters Patent is hereby corrected as shown below:

Column 5, line 14, "$C_nH_{2n}F_{2n+1}$. ($C_n$" should read --$C_nH_{2n}F_{2n+1}$, ($C_n$--.
Column 8, line 18, "0,021 moles" should read --0.021 moles--.
Column 10, line 23, "0,002 moles" should read --0.002 moles--.
Column 11, lines 60-66, lines 18-15), "$R_5=N$" should read --$R_6=N$--; "$R_{19}=C$" should read --$R_{10}=C$--; "$R_{15}=H$" should read --$R_{16}=H$--; and "$R_{29}=F$" should read --$R_{20}=F$--.

Column 17, line 42, "ethyl 3',5'-dimethyl" should read --ethyl 3,5-dimethyl--.
Column 23, line 53, "Ann Chem 718" should read --Ann. Chem. 718--.
Column 24, line 39, "2.1s (s.3H)" should read --2.18 (s, 3H)--.
Column 24, line 44, "$\delta$ 9.35 (S, 1H)" should read --$\delta$ 9.35 (s, 1H)--.
Column 25, line 39, "20 ml) The" should read --20 ml. The--.
Column 25, line 41, "1175 ml" should read --175 ml--.
Column 27, line 51, "114°C. IR" should read --114°C., IR--.
Column 27, line 52, "chloroform was chloroform" should read --chloroform was treated dropwise with an equimolar amount of bromine in chloroform--.
Column 28, line 59, "W=X=Z" should read --W=Y=Z--.
Column 28, line 66, "derivative m, RE" should read --derivative 7m, RE--.
Column 39, line 66, "the 0,004 µg/ml" should read --the 0.004 µg/ml--.

UNITED STATES PATENT AND TRADEMARK OFFICE
CERTIFICATE OF CORRECTION

PATENT NO. : 5,446,157
DATED : August 29, 1995
INVENTOR(S) : Lee Roy Morgan, et al.

It is certified that error appears in the above-indentified patent and that said Letters Patent is hereby corrected as shown below:

Column 42, line 33, "R" should read --$R_1$--.

Signed and Sealed this

Thirteenth Day of February, 1996

*Attest:*

BRUCE LEHMAN

*Attesting Officer*   *Commissioner of Patents and Trademarks*